(12) United States Patent
Shachar et al.

(10) Patent No.: US 6,911,198 B2
(45) Date of Patent: Jun. 28, 2005

(54) METHOD AND PHARMACEUTICAL COMPOSITION FOR TREATING INFLAMMATION

(75) Inventors: Idit Shachar, Ramat Gan (IL); Liat Flaishon, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 173 days.

(21) Appl. No.: 09/953,206

(22) Filed: Sep. 17, 2001

(65) Prior Publication Data

US 2003/0053985 A1 Mar. 20, 2003

(51) Int. Cl.[7] .................. A61K 38/21; A61K 45/00
(52) U.S. Cl. ..................... 424/85.5; 424/85.4
(58) Field of Search ............... 424/85.4, 85.5, 424/85.2

(56) References Cited

U.S. PATENT DOCUMENTS

| | | | |
|---|---|---|---|
| 4,921,697 A | | 5/1990 | Peterlik et al. |
| 5,145,677 A | * | 9/1992 | von Eichborn et al. .... 424/85.5 |
| 6,121,247 A | | 9/2000 | Huang et al. |

FOREIGN PATENT DOCUMENTS

| | | |
|---|---|---|
| WO | 01/23006 | 4/2001 |
| WO | 01/34180 | 5/2001 |

OTHER PUBLICATIONS

Paulnock et al., J. Interferon Res. 1989, vol. 9, pp. 457–473.*

Melmon et al., Principles of Therapeutics, pp. 40–55, in Goodman and Gilman's The Pharmacological Basis of Therapeutics, 1980.*

ACTIMMUNE package insert, 2003.*

Placebo–Associated Remissions in a Multicentre, Randomized, Double–Blind Trial of Interferon γ–1 b for the Treatment of Metastatic Renal Cell Carcinoma, Elhilali et al., BJU International, 2000, 86, pp 613–618.

Complete Response of Metastatic Renal Cell Carcinoma to Low–Dose Interferon–γ Treatment, Otto, et al., Cancer Immunol Immunother, 1995, 40: pp 115–118.

Renal Cell Carcinoma and Interferon at the Millennium, Pastore, et al., Cancer Investigation, 19(3) 2001, pp 281–291.

The Treatment of Metastatic Renal Cell Carcinoma Patients with Recombinant Human Gamma Interferon, Small, et al., Cancer J. Sci. Am., 1998, May–Jun., 4(3), 155–6.

A Preliminary Study of Long–Term Treatment with Interferon Gamma–1 b and Low–Dose Prednisolone in Pateitns with Idiopathic Pulmonary Fibrosis, Ziesche, et al., The New England Journal of Medicine, Oct. 21, 1999, vol. 341, No. 17, pp 1264–1269.

* cited by examiner

*Primary Examiner*—Janet Andres
(74) *Attorney, Agent, or Firm*—G.E. Ehrlich (1995) Ltd.

(57) ABSTRACT

A method of treating an inflammation in a subject in need thereof is disclosed. The method comprises locally or systemically administering to the subject IFN-γ in an amount so as to achieve an IFN-γ bulk tissue concentration at a site of inflammation of 1–8,000 units per kilogram body weight, thereby ameliorating the inflammation.

22 Claims, 22 Drawing Sheets

Fig. 1a Control

Fig. 1g IgM

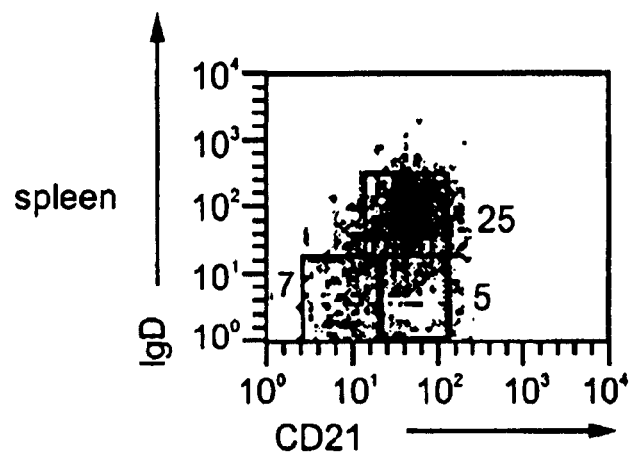
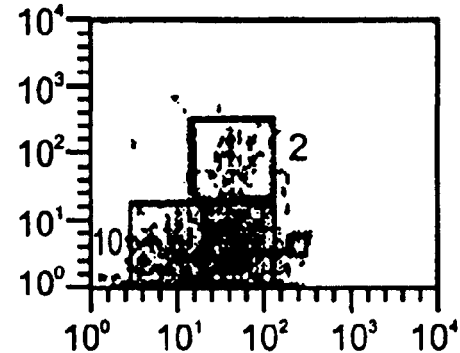
Fig. 1i    Fig. 1j
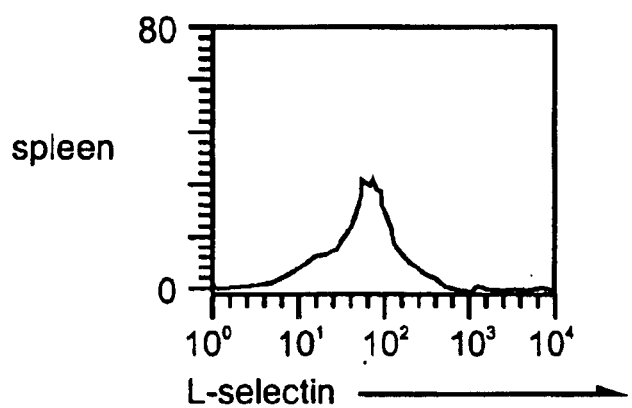
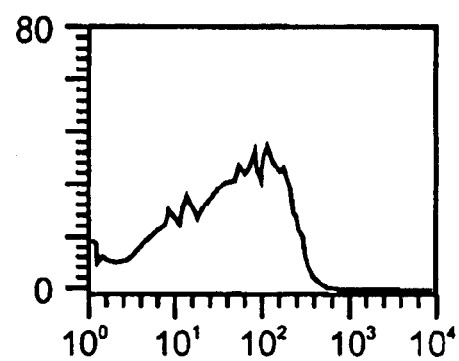
Fig. 1k    Fig. 1l

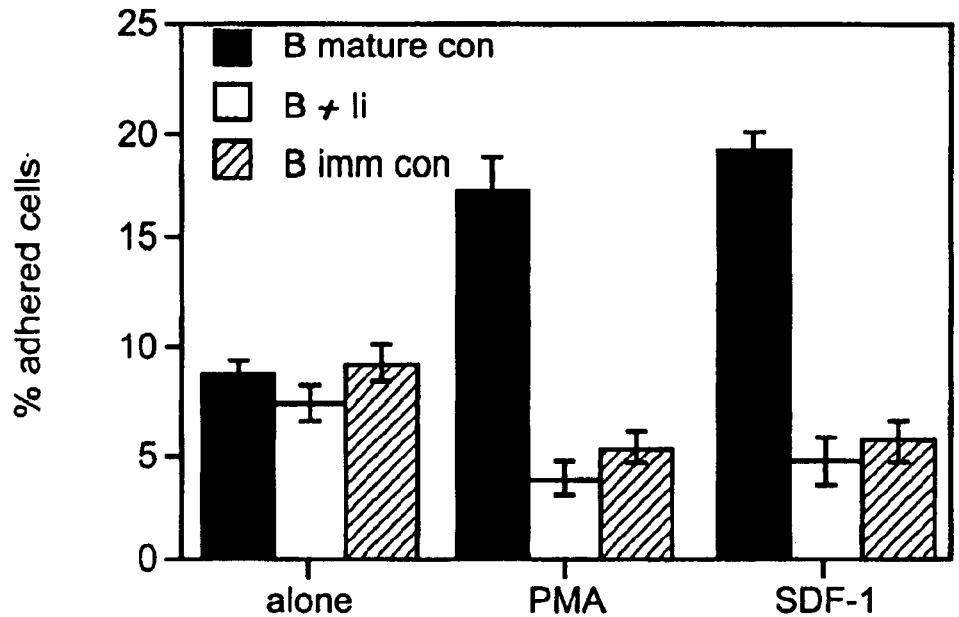
Fig. 2c
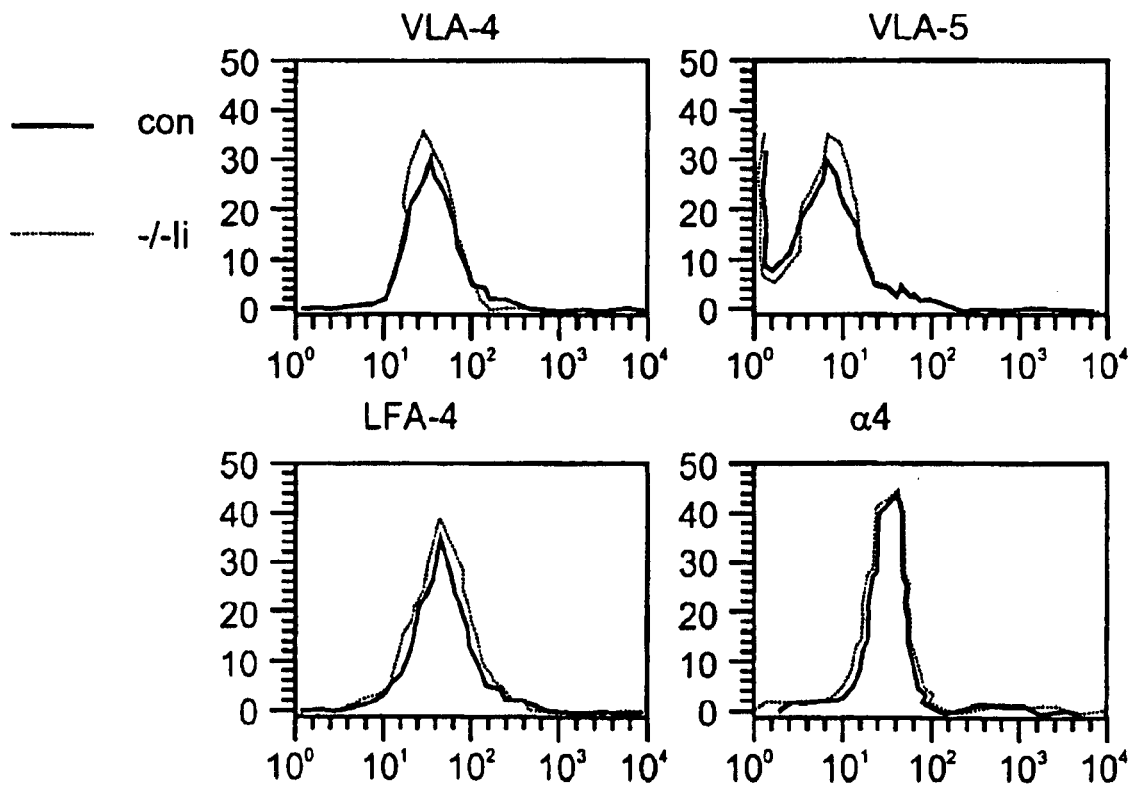
Fig. 2d  Fig. 2e
Fig. 2f  Fig. 2g

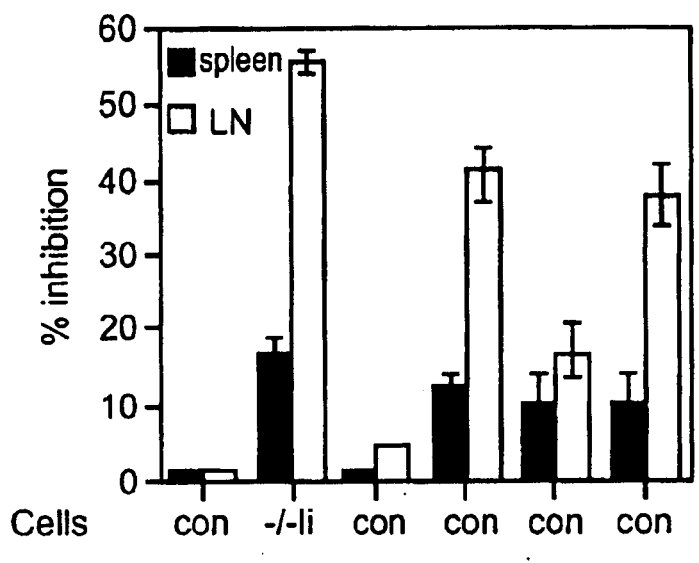
Fig. 5a
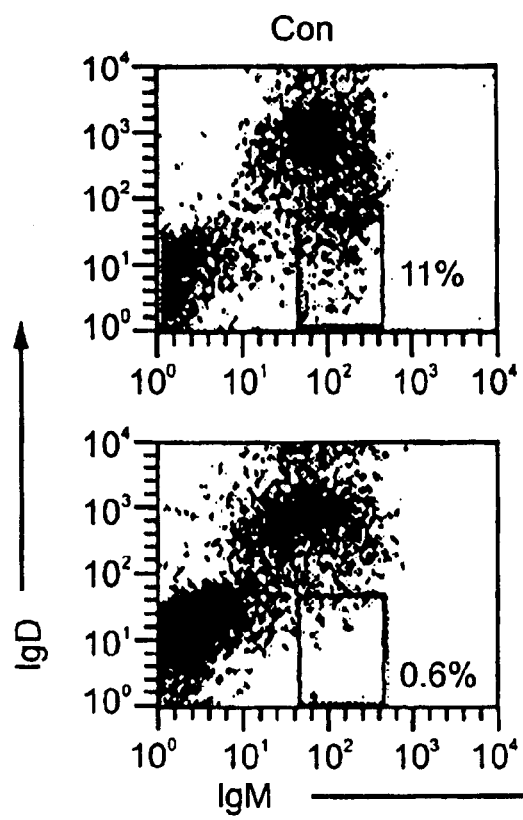
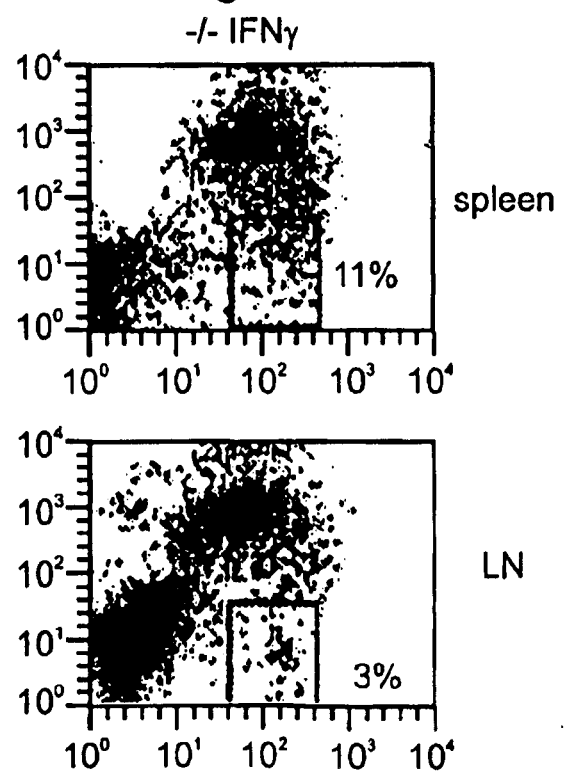
Fig. 5b  Fig. 5c
Fig. 5d  Fig. 5e

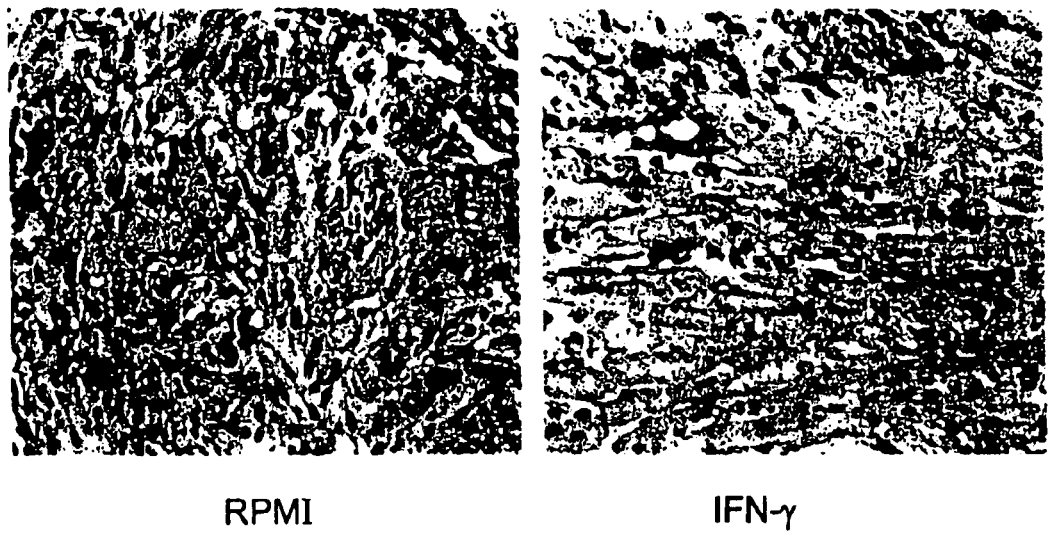
RPMI  
Fig. 8b
IFN-γ  
Fig. 8c
Control  
Fig. 9a
OVA  
Fig. 9b
OVA + IFN  
Fig. 9c Control

TNBS

TNBS + IFN

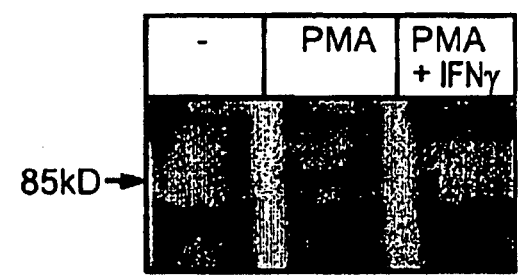
Fig. 13c
Fig. 14a
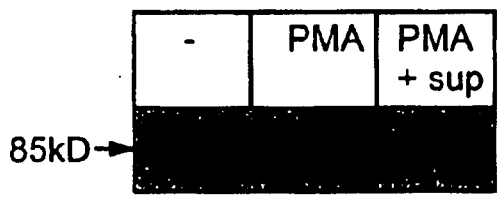
Fig. 14b
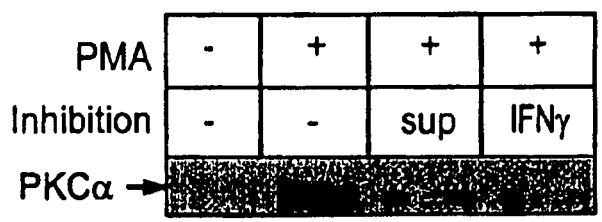
Fig. 14c
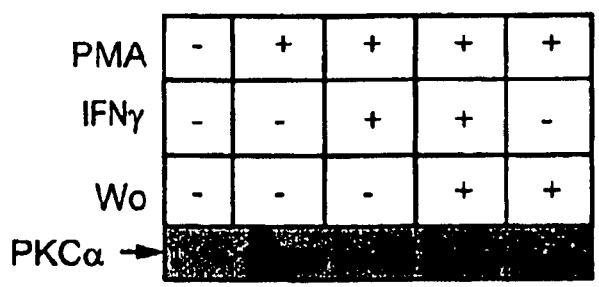
Fig. 14d
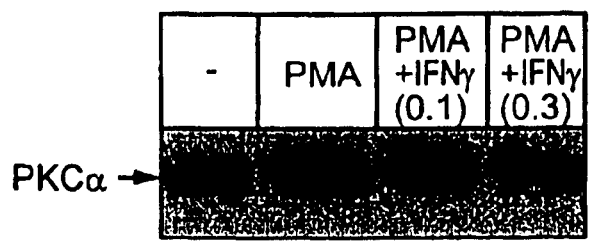
Fig. 14e

METHOD AND PHARMACEUTICAL COMPOSITION FOR TREATING INFLAMMATION

FIELD AND BACKGROUND OF THE INVENTION

The present invention relates in general to methods and pharmaceutical compositions for treating inflammation, and more particularly, to a method and pharmaceutical composition for downregulating adhesion and migration of lymphocytes and, specifically, to the administration of ultra-low dosages of interferon gamma (IFN-γ) to treat a variety of immunopathological states which are accompanied by inflammation, such as, but not limited to, autoimmune disease, allergy, inflammation and graft rejection.

Many lymphocyte-mediated immune processes require adhesion of lymphocytes to the ECM. Such adhesion is critical, for example, for B and T lymphocyte extravasation and migration during differentiation, activation, proliferation and effector function during both normal and pathological immune processes. As such, selectively interfering with adhesion and migration of lymphocytes can be directly and effectively applied towards treatment of disorders involving lymphocyte-mediated pathogenesis.

Specific Immunity:

The specific arm of the immune system employs B and T lymphocytes to recognize and eliminate foreign antigens, such as foreign microorganisms, foreign substances or allogeneic cells, while remaining unresponsive to self antigens. Targeting of specific foreign antigens and elimination of foreign bodies displaying these is mediated via B and T lymphocytes which, following somatic gene rearrangement and clonal selection, respectively express antibodies specific to a particular foreign antigen or T cell receptors (TCRs) specific to a particular major histocompatibility complex (MHC)-foreign peptide complex. The humoral arm of the immune system thus employs antibodies to eliminate, for example, bacteria and foreign substances, whereas the cellular arm of the immune system employs T lymphocytes to eliminate, for example, virus- or parasite-infected cells, cells expressing mutated self-antigens, such as tumor cells or allogeneic cells.

Trafficking of Lymphocytes During Immune Responses

During the processes of immune surveillance and specific immune responses, lymphocytes extravasate and migrate to secondary lymphoid organs, such as lymph nodes (LNs), for antigen-specific activation after which these migrate to the sites of inflammation for execution of effector functions against foreign pathogens. Extravasation of lymphocytes to such sites occurs through specialized high endothelial venules (HEV) via recognition of organ-specific adhesion molecules by counter-receptors, such as integrins, expressed on lymphocytes (Bradley, L., and Watson, S. R. Curr. Opin. Immunol. 1996, 8:312; Imhof, B. A., and Dunon, D. Adv. Immunol. 1995, 58:345). These processes involve multiple adhesion steps regulated via a combinatorial series of molecular events.

Continuous recirculation of lymphocytes to organized lymphoid tissue or to sites of antigen-presentation, such as LNs, is necessary for the development of primary immune responses to foreign antigen by lymphocytes and such recirculation from one anatomic compartment to another is critically dependent on adhesive interactions of lymphocytes with endothelium and with the extracellular matrix (ECM) for extravasation and migration within tissues, such as sites of inflammation, respectively.

The process of B cell development also involves distinct trafficking patterns and thus is also critically dependent on regulation of adhesion of B lymphocytes to endothelium and to ECM. Immature B cells initially differentiate in the bone marrow from which they exit to the periphery and selectively migrate into the spleen to complete their maturation. While in transit to the spleen, specific mechanisms prevent the entry into and/or retention of immature B cells in sites of antigen-presentation, such as sites of inflammation or secondary lymphoid organs, such as LNs. This is due to the fact that maturation of B cells occurs in anatomic compartments in which auto-antigens induce the clonal deletion of autoreactive immature B cells. Thus, such cells are prevented from entering sites of antigen-presentation so as to prevent deletion of foreign antigen-reactive clones.

The specific mechanisms of lymphocyte trafficking during immune responses are best characterized for T cells, as detailed below.

Non-activated T lymphocytes traffic through the T cell areas of secondary lymphoid organs, such as LNs, where they encounter antigen presented by dendritic cells (DCs), thereby triggering activation of antigen-specific T cells (Butcher, E. C., and Picker, L. J. Science 1996, 272:60; Banchereau, J., and Steinman, R. M. Nature 1998, 392:245). In the presence of polarizing cytokines, activated T lymphocytes acquire effector functions and differentiate into Th1 or Th2 subtypes displaying characteristic cytokine production profiles and mediating pro-inflammatory and allergic types of responses, respectively (Abbas, A. K. et al., Nature 1996, 383:787; O'Garra, A. Immunity 1998, 8:275). Such differentiated T cells downregulate LN homing receptors and upregulate specific tissue homing receptors (Xie, H.et al., J. Exp. Med. 1999, 189:1765; Potsch, C. et al., Eur. J. Immunol. 1999, 29:3562; Campbell, J. J., and Butcher, E. C. Curr. Opin. Immunol. 2000, 12:336; Sallusto, F. et al., Annu. Rev. Immunol. 2000, 18:593) resulting in Th1 and Th2 cells exhibiting distinct migratory profiles in vivo (Austrup, F. et al., Nature 1997, 385:81; Randolph, D. A. et al., Science 1999, 286:2159).

During immune responses to pathogenic insult, foreign antigens present in affected tissues are taken up by antigen-presenting DCs which migrate to sites of antigen-presentation, such as LNs. Meanwhile, components of the non-specific cellular immune system, such as neutrophils and other granulocytes, initiate inflammation by, for example, releasing pro-inflammatory molecules, such as chemokines and cytokines which activate local endothelial cells to upregulate expression of lymphocyte-specific adhesion molecules, such as immunoglobulin superfamily ligands. In sites of antigen-presentation, such as LNs, DCs presenting foreign antigens activate antigen-specific lymphocytes. Activated lymphocytes then upregulate adhesion molecules, such as integrins specific for activated endothelial cells (ECs), exit to the circulation and extravasate at sites of inflammation.

In the circulation, transient interactions between lymphocytes and endothelium enable lymphocyte tethering and rolling along the endothelial wall. During this rolling phase, lymphocytes are activated by intracellular signals generated by engaged adhesion molecules, such as selectins and chemokine receptors, which transduce signals promoting firm adhesion between integrin molecules, expressed on lymphocytes, and their immunoglobulin superfamily ligands expressed on the endothelial wall. Such adherent lymphocytes then extravasate through the intercellular margins of the endothelium and migrate, via adhesion-disruption cycles, through the ECM to reach foreign-antigen containing inflamed tissue wherein effector functions are performed (Butcher, E. C. Cell 1991, 67:1033; Shimizu, Y., W. et al., Immunol. Today 1992, 13:106; Mackay, C. R., and B. A. Imhof. Immunol. Today 1993, 14:99; Schall, T. J., and K. B. Bacon. Curr. Opin. Immunol. 1994, 6:865; Hogg, N., and C. Berlin. Immunol. Today 1995, 16:327; Imhof, B. A., and D. Dunon. Adv. Immunol. 1995, 58:345; Butcher, E. C., and J. Picker. Science 1996, 272:60; Springer, T. Annu. Rev. Physiol. 1995, 57:827).

The trafficking signals directing activated effector T cells to peripheral tissues are organ-specific and are distinct for the different subgroups of T cells. For example, naive T cells express CD62 ligand (CD62L) and CC chemokine receptor 7 (CCR7), which are required for HEV extravasation (Springer, T. A. Cell 1994, 76:301; Cyster, J. G. Science 1999, 286:2098; Stein, J. V. et al., J. Exp. Med. 2000, 191:61; Forster, R. et al., Cell 1999, 99:23). Upon foreign antigen encounter at sites of inflammation, activated lymphocytes release cytokines and chemokines which amplify the inflammatory cascade thereby increasing vascular and ECM permeability thus facilitating infiltration of effectors to inflamed sites of foreign pathogen infiltration. Such inflammatory processes normally result in a certain amount of tissue destruction which, when appropriately regulated, is tolerated by the body as a reversible consequence of optimal immune responses.

Thus, adhesion of lymphocytes to endothelium and the ECM is critical to extravasation and migration during processes such as lymphocyte maturation, antigen-specific activation and effector responses against foreign antigens at sites of inflammation.

Lymphocyte-Mediated Disorders:

Although lymphocyte-mediated immune processes normally serve to allow the immune system to fight foreign pathogens, in certain contexts such immune processes can lead to pathological states referred to as hypersensitivity diseases. Alternatively, transplantation of foreign cells, tissues or organs or surgically implanted prosthetic devices can also elicit undesirable immune responses against such implants in recipients subjected to such therapeutic interventions. In such diseases, lymphocytic infiltration into tissues and the consequences thereof, such as cytokine production, significantly contribute to undesirable sequelae, such as acute tissue injury, resulting from uncontrolled inflammation.

Such uncontrolled inflammation may be a result of antibody-mediated diseases such as allergy (immediate hypersensitivity) or immune complex deposition. Alternatively, uncontrolled inflammation may be a result of T lymphocyte-mediated diseases such as contact dermatitis and drug eruptions (delayed hypersensitivity). Infection or cancer may also result in uncontrolled inflammation.

Importantly, deregulated immune responses may specifically target self-antigens, either idiopathically, as a result of cross-reactivity with foreign antigen or, alternately, immunity directed against foreign antigens may cause damage to specific tissues to which such foreign antigens have a specific affinity.

Such hypersensitivity diseases have been implicated in an extremely broad range of autoimmune diseases including systemic, cutaneous, rheumatoid, cardiovascular, gastrointestinal, hepatic, reproductive, glandular, neurological, muscular, nephric and connective tissue autoimmune diseases, as described in the Preferred Embodiments section.

Role of Lymphocytes in Transplantation Failure:

Immune reactions may also be deleterious in the context of therapeutic tissue transplantation. For example, T lymphocytes are responsible for transplantation-related immunopathologies such as allograft rejection (Krensky A. et al., N Engl J Med. 1990 Feb. 22; 322 (8):510) and GVHD (Theobald, M. Transfus Sci 1994 September; 15 (3):189) which are the major causes of transplantation failure. In allograft rejection and in GVHD, respectively, immune responses are mediated by T cells of the host or of the donor, respectively, which extravasate and migrate into donor and host tissues, respectively, to induce disease. In the case of graft rejection, host T lymphocytes also migrate into secondary lymphoid organs where they are primed against graft-derived allogeneic antigens.

Prior Art Therapy Using IFN-γ:

Satisfactory IFN-γ-based therapies for many diseases involving inflammation, such as autoimmune diseases, allergic diseases, transplantation failure and cancer, as described above, have yet to be developed. Prior art approaches of treating inflammation-related disorders using IFN-γ have employed administration of high levels of this cytokine, as described below.

Animal studies: The use of high levels of IFN-γ to regulate inflammatory processes has been attempted in animal models of autoimmune disease. In a murine asthma model, treatment of tracheal eosinophil and $CD4^+$ T cell infiltration was achieved using intraperitoneal administration of high levels of IFN-γ, at doses of 24,000 and 240,000 units per kilogram body weight administered per day, respectively, in response to ovalbumin (OVA) inhalation (Iwamoto, I. et al., J. Exp. Med. 1993, 177:573).

Human studies: Since high levels of IFN-γ were shown to be of potential therapeutic benefit in animal studies, such as the one described above, therapy employing high levels of IFN-γ has been attempted in human clinical trials for treatment of autoimmune disease. Such treatments, however, have been found to produce unacceptably severe side-effects in patients.

For example, in a clinical trial of long-term treatment of the inflammatory disease idiopathic pulmonary fibrosis, high levels of IFN-γ (33,000 units per kilogram body weight administered three times per week) were required in order to provide substantial therapeutic effect (Ziesche, R. et al., N. Engl. J. Med. 1999, 341:1264). All patients treated in this study, however, developed fever and chills and one-third experienced significant bone and muscle pain as a result of high-dose IFN-γ administration.

In an open pilot study employing IFN-γ therapy for treatment of another inflammatory disease, Crohn's disease, administration of high levels of IFN-γ (15,000 units/kg administered three times per week) led to a substantial decrease in Crohn's disease activity index in most patients, however, most patients did not finish the 12-week treatment course due to suboptimized dosages and an unacceptable incidence of side-effects (Debinski H. et al., Ital J Gastroenterol Hepatol 1997 October; 29(5):403). It should be noted that although the title of the latter publication refers to the employed dose of 15,000 units per kilogram body weight IFN-γ as being a "low" dose, the method of the present invention, as described in the Examples section, below, employs ultra-low doses of IFN-γ being at least two orders of magnitude lower than such doses.

The undesirable side-effects of high doses of IFN-γ were also demonstrated in a human clinical trial for treatment of metastatic renal cell carcinoma in which patients were treated with high levels of IFN-γ ($10^7$ units IFN-γ per $m^2$ per day for 5 days, administered every two weeks for four weeks, followed by repeated administration of such dose, three times a week for 2 weeks. A dose of $10^7$ units/$m^2$ corresponds to over 100,000 units per kg body weight in an average 60 kg human) (Griebel, P. et al., Int. Immunol. 1999, 11:1139). These patients experienced major side-effects including fever and chills (75%), anorexia and fatigue (75%), nausea and vomiting (80%), leukopenia (38%) and abnormal liver function (25%).

Thus, as a result of the significant side-effects of high-dose IFN-γ treatment described above, this cytokine is not currently employed therapeutically. The deleterious effects of high-dose IFN-γ may result from its potentiation of the effects of other pro-inflammatory mediators and upregulation of surface expression of MHC class II in monocytes, macrophages and dendritic cells, as well as of adhesion molecules in endothelial and epithelial cells (Barnes, P. J., and Lim, S. Mol. Med. Today 1998, 4:452).

There is thus a widely recognized need for, and it would be highly advantageous to have, a method of treatment of disease with IFN-γ devoid of the above limitations.

SUMMARY OF THE INVENTION

According to one aspect of the present invention there is provided a method of treating an inflammation in a subject in need thereof, the method comprising locally or systemically administering to the subject IFN-γ in an amount so as to achieve an IFN-γ bulk tissue concentration at a site of inflammation of 1–8,000 units per kilogram body weight, thereby ameliorating the inflammation.

According to further features in preferred embodiments of the invention described below, the bulk tissue concentration is 0.1–4,000 units per kilogram body weight.

According to still further features in the described preferred embodiments, the bulk tissue concentration is 0.2–2,000 units per kilogram body weight.

According to still further features in the described preferred embodiments, the bulk tissue concentration is 0.5–1,000 units per kilogram body weight.

According to still further features in the described preferred embodiments, the bulk tissue concentration is 1–500 units per kilogram body weight.

According to still further features in the described preferred embodiments, the bulk tissue concentration is 2–240 units per kilogram body weight.

According to still further features in the described preferred embodiments, the bulk tissue concentration is 4–240 units per kilogram body weight.

According to still further features in the described preferred embodiments, the concentration is sufficiently low so as to avoid unwanted side-effects associated with IFN-γ administration.

According to still further features in the described preferred embodiments, the unwanted side-effects are selected from the group consisting of fever, chills, flu symptoms, bone pain, muscle pain, anorexia, fatigue, nausea, vomiting, leukopenia, diarrhea, fatigue, abnormal liver function, black, tarry stools; blood in urine, blood in stools, confusion, cough, hoarseness, loss of balance control, mask-like face, painful urination, difficult urination, pinpoint red spots on skin, shuffling walk, stiffness of arms, stiffness of legs, trembling of hands, shaking of hands, trembling of fingers, shaking of fingers, trouble in speaking, trouble in swallowing, trouble in thinking, trouble in concentrating, trouble in walking, unusual bleeding, unusual bruising, general feeling of discomfort, general feeling of illness, headache, skin rash, unusual tiredness, back pain, side-pain, dizziness, joint pain, loss of appetite and weight loss.

According to still further features in the described preferred embodiments, the inflammation is associated with an inflammatory disease, disorder or condition.

According to still further features in the described preferred embodiments, the inflammatory disease is selected from the group consisting of chronic inflammatory disease and acute inflammatory disease.

According to still further features in the described preferred embodiments, the inflammation is associated with hypersensitivity.

According to still further features in the described preferred embodiments, the hypersensitivity is selected from the group consisting of Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and delayed type hypersensitivity.

According to still further features in the described preferred embodiments, the delayed type hypersensitivity is selected from the group consisting of contact dermatitis and drug eruption.

According to still further features in the described preferred embodiments, the T lymphocyte-mediated hypersensitivity is selected from the group consisting of helper T lymphocyte mediated hypersensitivity and cytotoxic T lymphocyte mediated hypersensitivity.

According to still further features in the described preferred embodiments, the helper T lymphocyte-mediated hypersensitivity is selected from the group consisting of $T_h1$ lymphocyte mediated hypersensitivity and $T_h2$ lymphocyte mediated hypersensitivity.

According to still further features in the described preferred embodiments, the inflammation is associated with autoimmune disease.

According to still further features in the described preferred embodiments, the autoimmune disease is selected from the group consisting of cardiovascular disease, rheumatoid disease, glandular disease, gastrointestinal disease, cutaneous disease, hepatic disease, neurological disease, muscular disease, nephric disease, disease related to reproduction, connective tissue disease and systemic disease.

According to still further features in the described preferred embodiments, the cardiovascular disease is selected from the group consisting of occlusive disease, atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity in Chagas' disease and anti-helper T lymphocyte autoimmunity.

According to still further features in the described preferred embodiments, the rheumatoid disease is selected from the group consisting of rheumatoid arthritis and ankylosing spondylitis.

According to still further features in the described preferred embodiments, the glandular disease is selected from the group consisting of pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

According to still further features in the described preferred embodiments, the gastrointestinal disease is selected from the group consisting of colitis, ileitis, Crohn's disease, chronic inflammatory intestinal disease and celiac disease.

According to still further features in the described preferred embodiments, the cutaneous disease is selected from the group consisting of autoimmune bullous skin disease, pemphigus vulgaris, bullous pemphigoid and pemphigus foliaceus.

According to still further features in the described preferred embodiments, the hepatic disease is selected from the group consisting of autoimmune hepatitis and primary biliary cirrhosis.

According to still further features in the described preferred embodiments, the neurological disease is selected from the group consisting of neurodegenerative disease, multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis and stiff-man syndrome.

According to still further features in the described preferred embodiments, the muscular disease is selected from the group consisting of autoimmune myositis, primary Sjogren's syndrome and smooth muscle autoimmune disease.

According to still further features in the described preferred embodiments, the nephric disease is autoimmune interstitial nephritis.

According to still further features in the described preferred embodiments, the disease related to reproduction is repeated fetal loss.

According to still further features in the described preferred embodiments, the connective tissue disease is selected from the group consisting of autoimmune ear disease and autoimmune disease of the inner ear.

According to still further features in the described preferred embodiments, the systemic disease is selected from the group consisting of systemic lupus erythematosus and systemic sclerosis.

According to still further features in the described preferred embodiments, the inflammation is associated with an infectious disease.

According to still further features in the described preferred embodiments, the infectious disease is selected from the group consisting of chronic infectious disease, subacute infectious disease, acute infectious disease, viral disease, bacterial disease, protozoan disease, parasitic disease, fungal disease, mycoplasma disease and prion disease.

According to still further features in the described preferred embodiments, the inflammation is associated with a disease associated with transplantation of a graft.

According to still further features in the described preferred embodiments, the disease is selected from the group consisting of graft rejection, chronic graft rejection, subacute graft rejection, hyperacute graft rejection, acute graft rejection and graft versus host disease.

According to still further features in the described preferred embodiments, the graft is selected from the group consisting of a syngeneic graft, an allograft and a xenograft.

According to still further features in the described preferred embodiments, the graft is selected from the group consisting of a cellular graft, a tissue graft, an organ graft and an appendage graft.

According to still further features in the described preferred embodiments, the cellular graft is selected from the group consisting of a stem cell graft, a progenitor cell graft, a hematopoietic cell graft, an embryonic cell graft and a nerve cell graft.

According to still further features in the described preferred embodiments, the tissue graft is selected from the group consisting of a skin graft, a bone graft, a nerve graft, an intestine graft, a corneal graft, a cartilage graft, a cardiac tissue graft, a cardiac valve graft, a dental graft, a hair follicle graft and a muscle graft.

According to still further features in the described preferred embodiments, the organ graft is selected from the group consisting of a kidney graft, a heart graft, a skin graft, a liver graft, a pancreatic graft, a lung graft and an intestine graft.

According to still further features in the described preferred embodiments, the appendage graft is selected from the group consisting of an arm graft, a leg graft, a hand graft, a foot graft, a finger graft, a toe graft and a sexual organ graft.

According to still further features in the described preferred embodiments, the inflammation is associated with an allergic disease.

According to still further features in the described preferred embodiments, the allergic disease is selected from the group consisting of asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to still further features in the described preferred embodiments, the inflammation is associated with a neurodegenerative disease.

According to still further features in the described preferred embodiments, the inflammation is associated with a cardiovascular disease.

According to still further features in the described preferred embodiments, the inflammation is associated with a gastrointestinal disease.

According to still further features in the described preferred embodiments, the inflammation is associated with a tumor.

According to still further features in the described preferred embodiments, the tumor is selected from the group consisting of a malignant tumor, a benign tumor, a solid tumor, a metastatic tumor and a non-solid tumor.

According to still further features in the described preferred embodiments, the inflammation is associated with septic shock.

According to still further features in the described preferred embodiments, the inflammation is associated with anaphylactic shock.

According to still further features in the described preferred embodiments, the inflammation is associated with toxic shock syndrome.

According to still further features in the described preferred embodiments, the inflammation is associated with cachexia.

According to still further features in the described preferred embodiments, the inflammation is associated with necrosis.

According to still further features in the described preferred embodiments, the inflammation is associated with gangrene.

According to still further features in the described preferred embodiments, the inflammation is associated with a prosthetic implant.

According to still further features in the described preferred embodiments, the prosthetic implant is selected from the group consisting of a breast implant, a silicone implant, a dental implant, a penile implant, a cardiac implant, an artificial joint, a bone fracture repair device, a bone replacement implant, a drug delivery implant, a catheter, a pacemaker and a respirator tube.

According to still further features in the described preferred embodiments, the inflammation is associated with menstruation.

According to still further features in the described preferred embodiments, the inflammation is associated with an ulcer.

According to still further features in the described preferred embodiments, the ulcer is selected from the group consisting of a skin ulcer, a bed sore, a gastric ulcer, a peptic ulcer, a buccal ulcer, a nasopharyngeal ulcer, an esophageal ulcer, a duodenal ulcer and a gastrointestinal ulcer.

According to still further features in the described preferred embodiments, the inflammation is associated with an injury.

According to still further features in the described preferred embodiments, the injury is selected from the group consisting of an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound.

According to still further features in the described preferred embodiments, the inflammation is a musculo-skeletal inflammation.

According to still further features in the described preferred embodiments, the musculo-skeletal inflammation is selected from the group consisting of a muscle inflammation, myositis, a tendon inflammation, tendinitis, a ligament inflammation, a cartilage inflammation, a joint inflammation, a synovial inflammation, carpal tunnel syndrome and a bone inflammation.

According to still further features in the described preferred embodiments, the inflammation is selected from the group consisting of an idiopathic inflammation and an inflammation of unknown etiology.

According to still further features in the described preferred embodiments, the IFN-γ is administered in a pharmaceutical composition which includes a pharmaceutically acceptable carrier.

According to still further features in the described preferred embodiments, the pharmaceutically acceptable carrier adapts the composition for administration by a route selected from the intranasal, transdermal, intradermal, oral, buccal, parenteral, topical, rectal and inhalation route.

According to still further features in the described preferred embodiments, the carrier provides the IFN-γ in solution, suspension, emulsion, gel or skin pad.

According to still further features in the described preferred embodiments, the composition further includes a formulating agent selected from the group consisting of a suspending agent, a stabilizing agent and a dispersing agent.

According to another aspect of the present invention there is provided a pharmaceutical composition for treating an inflammation in a subject in need thereof, each dose-unit of the pharmaceutical composition comprising, as an active ingredient, IFN-γ in an amount of 1–800,000 units, thereby ameliorating the inflammation.

According to further features in preferred embodiments of the invention described below, the amount is of 2–400,000 units.

According to still further features in the described preferred embodiments, the amount is of 5–200,000 units.

According to still further features in the described preferred embodiments, the amount is of 10–100,000 units.

According to still further features in the described preferred embodiments, the amount is of 25–50,000 units.

According to still further features in the described preferred embodiments, the amount is of 60–21,600 units.

According to still further features in the described preferred embodiments, the inflammation is associated with an inflammatory disease, disorder or condition, the pharmaceutical composition is packaged and identified for treatment of an inflammatory disease, disorder or condition.

According to still further features in the described preferred embodiments, the inflammation is associated with hypersensitivity, the pharmaceutical composition is packaged and identified for treatment of hypersensitivity.

According to still further features in the described preferred embodiments, the inflammation is associated with autoimmune disease, the pharmaceutical composition is packaged and identified for treatment of autoimmune disease.

According to still further features in the described preferred embodiments, the inflammation is associated with transplantation of a graft, the pharmaceutical composition is packaged and identified for treatment of a disease associated with transplantation of a graft.

According to still further features in the described preferred embodiments, the inflammation is associated with an allergic disease, the pharmaceutical composition is packaged and identified for treatment of an allergic disease.

According to still further features in the described preferred embodiments, the inflammation is associated with a neurodegenerative disease, the pharmaceutical composition is packaged and identified for treatment of a neurodegenerative disease.

According to still further features in the described preferred embodiments, the inflammation is associated with a cardiovascular disease, the pharmaceutical composition is packaged and identified for treatment of a cardiovascular disease.

According to still further features in the described preferred embodiments, the inflammation is associated with a gastrointestinal disease, the pharmaceutical composition is packaged and identified for treatment of a gastrointestinal disease.

According to still further features in the described preferred embodiments, the inflammation is associated with a tumor, the pharmaceutical composition is packaged and identified for treatment of a tumor.

According to still further features in the described preferred embodiments, the inflammation is associated with septic shock, the pharmaceutical composition is packaged and identified for treatment of septic shock.

According to still further features in the described preferred embodiments, the inflammation is associated with anaphylactic shock, the pharmaceutical composition is packaged and identified for treatment of anaphylactic shock.

According to still further features in the described preferred embodiments, the inflammation is associated with toxic shock syndrome, the pharmaceutical composition is packaged and identified for treatment of toxic shock syndrome.

According to still further features in the described preferred embodiments, the inflammation is associated with cachexia, the pharmaceutical composition is packaged and identified for treatment of cachexia.

According to still further features in the described preferred embodiments, the inflammation is associated with necrosis, the pharmaceutical composition is packaged and identified for treatment of necrosis.

According to still further features in the described preferred embodiments, the inflammation is associated with gangrene, the pharmaceutical composition is packaged and identified for treatment of gangrene.

According to still further features in the described preferred embodiments, the inflammation is associated with a prosthetic implant, the pharmaceutical composition is packaged and identified for treatment of a prosthetic implant.

According to still further features in the described preferred embodiments, the inflammation is associated with menstruation, the pharmaceutical composition is packaged and identified for treatment of menstruation.

According to still further features in the described preferred embodiments, the inflammation is associated with an ulcer, the pharmaceutical composition is packaged and identified for treatment of an ulcer.

According to still further features in the described preferred embodiments, the inflammation is associated with an injury, the pharmaceutical composition is packaged and identified for treatment of an injury.

According to still further features in the described preferred embodiments, the inflammation is a musculo-skeletal inflammation, the pharmaceutical composition is packaged and identified for treatment of a musculo-skeletal inflammation.

According to still further features in the described preferred embodiments, the inflammation is associated with an idiopathic inflammation, the pharmaceutical composition is packaged and identified for treatment of an idiopathic inflammation.

According to still further features in the described preferred embodiments, the inflammation is associated with an inflammation of unknown etiology, the pharmaceutical composition is packaged and identified for treatment of an inflammation of unknown etiology.

According to still further features in the described preferred embodiments, the dose-unit achieves upon local or systemic administration an IFN-γ bulk tissue concentration at a site of inflammation of 1–8,000 units per kilogram body weight.

According to still further features in the described preferred embodiments, the IFN-γ bulk tissue concentration at a site of inflammation is of 1.5–4,000 units per kilogram body weight.

According to still further features in the described preferred embodiments, the IFN-γ bulk tissue concentration at a site of inflammation is of 2–2,000 units per kilogram body weight.

According to still further features in the described preferred embodiments, the IFN-γ bulk tissue concentration at a site of inflammation is of 2.5–1,000 units per kilogram body weight.

According to still further features in the described preferred embodiments, the IFN-γ bulk tissue concentration at a site of inflammation is of 3–500 units per kilogram body weight.

According to still further features in the described preferred embodiments, the IFN-γ bulk tissue concentration at a site of inflammation is of 3.5–240 units per kilogram body weight.

According to still further features in the described preferred embodiments, the IFN-γ bulk tissue concentration at a site of inflammation is of 4–240 units per kilogram body weight.

According to still further features in the described preferred embodiments, the pharmaceutical composition comprises, as an active ingredient, IFN-γ in an amount of 1–800,000 units, and a pharmaceutically acceptable carrier adapted for systemic administration.

According to yet another aspect of the present invention there is provided a pharmaceutical composition for treating an inflammation in a subject in need thereof, the pharmaceutical composition comprising, as an active ingredient, IFN-γ in an amount of 0.0002–8 units, and a pharmaceutically acceptable carrier adapted for local administration.

According to further features in preferred embodiments of the invention described below, the amount is of 0.0005–8 units.

According to still further features in the described preferred embodiments, the amount is of 0.001–8 units.

According to still further features in the described preferred embodiments, the amount is of 0.002–8 units.

According to still further features in the described preferred embodiments, the amount is of 0.004–8 units.

The present invention successfully addresses the shortcomings of the presently known configurations by providing a method of using IFN-γ, without risk of causing severe side-effects, for treating a disease, disorder or condition associated with, and/or accompanied by, inflammation.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a–d are histograms depicting cytofluorometric analysis of control and $Ii^{-/-}$ splenocytes or pooled LN cells stained with anti-B220. Histograms show the percentage of B cells in each population.

FIGS. 1e–h are dot-plots depicting cytofluorometric analysis of splenocytes and LN cells from control (FIGS. 1e and 1g) and Ii$^{-/-}$ (FIGS. 1f and 1h) mice triple-stained with anti-B220, anti-IgM and anti-IgD antibody. The analysis demonstrates expression of IgM and IgD on B220$^+$ gated cells. Boxes mark the immature IgD$^{low}$ population.

FIGS. 1i–j are dot-plots depicting cytofluorometric analysis of CD21 surface expression in B220$^+$ cells of control and Ii$^{-/-}$ mice (FIGS. 1i and 1j, respectively). The differences in IgD expression between FIGS. 1e–h and FIGS. 1i–j fall within the standard deviation and thus are not significant.

FIGS. 1k–l are histograms depicting cytofluorometric analysis of bulk splenocytes of control and Ii$^{-/-}$ mice (FIGS. 1k and 1l, respectively) double-stained with anti-B220 and anti-L-selectin antibody. Histograms depict expression of L-selectin on B220$^+$ cells.

FIG. 2c is a histogram depicting the percentage of mature IgD$^+$ B cells from control mice (B mature con), immature Ii$^{-/-}$ B cells (B Ii$^{-/-}$) and immature IgD$^-$ B cells from control mice (B imm con) adhering to FN. One representative experiment out of three is depicted.

FIGS. 2d–g are histograms depicting flow cytofluorometric analysis of integrin expression on immature and mature B cells. Control and Ii$^{-/-}$ splenocytes were double-stained with anti-B220 and either anti-VLA-4 (FIG. 2d), -VLA-5 (FIG. 2e), -LFA-1 (FIG. 2f) or α4β7 (FIG. 2g). Histograms depict B220$^+$-gated cells and depict an overlay of the expression levels of the different integrins on control (light-colored outline) and Ii$^{-/-}$ (dark-colored outline) B cells.

FIG. 5a is a histogram depicting the percentage of control B cells migrating to spleen or LN following treatment with conditioned medium collected from control (sup con) or Ii$^{-/-}$ (sup–/–Ii) B cells, B cell-conditioned medium treated with anti-IFN-γ antibody (sup–/–Ii α-IFN) or ultra-low levels of IFN-γ (1 unit/ml, IFN). The proportion of control cells homing to control spleen or LN in the absence of inhibitory treatment was designated as 100%. Percent inhibition of migration was defined as indicated in Materials and Methods. The data shown represent the average of 3 experiments.

FIGS. 5b–e are dot-plots depicting immunofluorescent flow cytometric analysis of IgD and IgM surface expression in bulk splenocytes (FIGS. 5b–c) and bulk LN cells (FIGS. 5d–e) of control (FIGS. 5b and 5d) and IFN-γ$^{-/-}$ (FIGS. 5c and 5e) mice. The percentages of immature cells per total B cell populations are indicated. The data depict one representative mouse out of 4 analyzed.

FIG. 7b). One group of mice was treated with dexamethazone (dexa), an anti-inflammatory agent, as a positive control. Swelling inhibition=(thickness of treated ear in treated mouse)−(thickness of untreated ear in treated mouse)/(swelling without treatment)×100.

FIGS. 8a–c depict inhibition of mononuclear cell infiltration into a kidney allograft following treatment with ultra-low levels of IFN-γ. FIG. 8a is a plot depicting relative infiltration of mononuclear cells into kidney tissue obtained from C3H (Syn) or Balb/c (Allo) mice on Days 4 and 7 following transplantation thereof under the kidney capsule of C3H hosts. The C3H hosts were subjected to three injections/wk of IFN-γ (5 units/day) for 1 wk prior to receiving the graft and every other day following transplantation, until time of sacrifice. Control animals (Allo) received injections of RPMI. Mononuclear infiltration was scored by counting cells in at least four high-power fields (×100) of the renal graft, as follows: 0-no infiltration, 1-low infiltration, 2-infiltration only to the allograft borders, 3-massive infiltration. Representative high-power fields depicting histological analysis of mononuclear cell infiltration into Balb/c-derived kidney tissue 5 days post-transplantation into C3H mice treated with RPMI or low-level IFN-γ are shown in FIGS. 8b–c, respectively.

FIGS. 9a–c are photomicrographs depicting IFN-γ mediated inhibition of eosinophilic infiltration into asthmatic lung. Shown are untreated Balb/c mice (FIG. 9a) and Balb/c mice sensitized with aerosolized OVA alone (FIG. 9b) or in combination with 5 units/d IFN-γ (FIG. 9c). Eosinophilic infiltration was detected via Hand E staining of formalin-fixed lung tissue.

FIG. 13c depicts Western immunoblotting analysis of Akt protein phosphorylation in PMA-stimulated 70Z/3 cells cultured in FN-coated tissue culture dishes in the presence of ultra-low levels of IFN-γ. Aliquots of $10^7$ cells were pre-incubated in the presence of absence of ultra-low levels of IFN-γ (0.1 unit/ml) for 30 min, stimulated with PMA for 5 min following which the cells were lysed and lysate proteins were subjected to Western immunoblotting analysis using anti-p-Akt antibody.

FIGS. 14a–b are Western immunoblotting analyses depicting phosphorylated 85 kD protein in 70Z/3 cells pre-incubated for 30 min in the presence of ultra-low levels of IFN-γ (0.1 unit/ml) (FIG. 14a) or immature B cell-conditioned medium (sup) (FIG. 14b) and plated for 5 min in FN-coated plastic tissue culture dishes in the presence of PMA. Lanes represent blotted protein from $10^7$ cells probed with anti-p-tyr antibodies.

FIGS. 14c–d depict Western immunoblotting analyses of phosphorylated PKCα protein in PMA-stimulated 70Z/3 cells pre-incubated for 30 min in the presence of ultra-low levels of IFN-γ (0.1 unit/ml) or immature B cell-conditioned medium (sup) (FIG. 14c) or in the presence of ultra-low levels of IFN-γ (0.1 unit/ml) in the presence of wortmannin (Wo) (FIG. 14d) and plated for 5 min in FN-coated plastic tissue culture dishes in the presence of PMA. Lanes represent protein from $10^7$ cells immunoprecipitated with anti-p-tyr antibody and developed with anti-PKCα antibody.

FIGS. 14e–f depict expression of PKCα protein in purified membrane of 70Z/3 cells in the presence of low-levels of IFN-γ. FIG. 14e depicts Western immunoblotting analysis of PKCα protein in purified membrane of 70Z/3 cells incubated in the presence of IFN-γ (0.1 or 0.3 units/ml) and FIG. 14f is a histogram depicting densitometric analysis of PKCα expression in the Western blot shown in FIG. 14e.

DESCRIPTION OF THE PREFERRED EMBODIMENTS

Figure 1D:
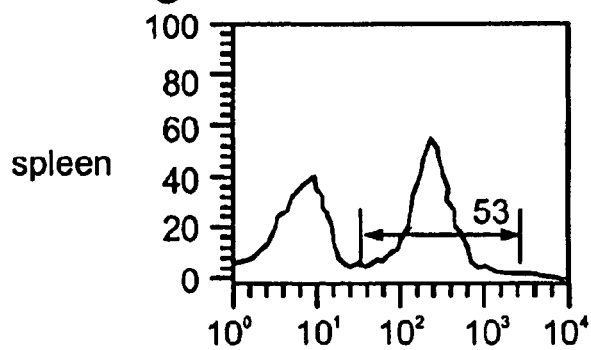
Figure 1D:
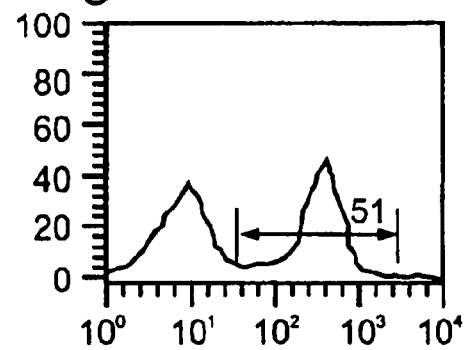
Figure 1D:
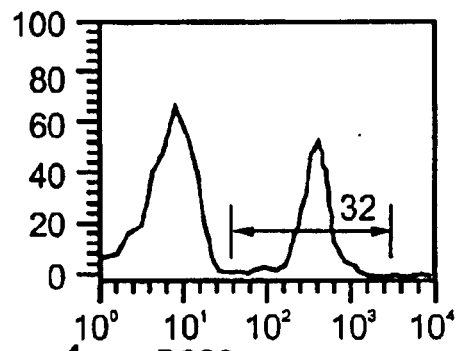
Figure 1D:
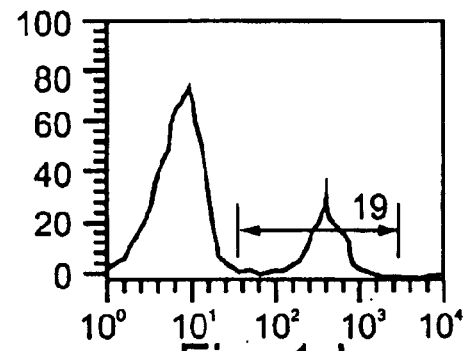
Figure 1E:
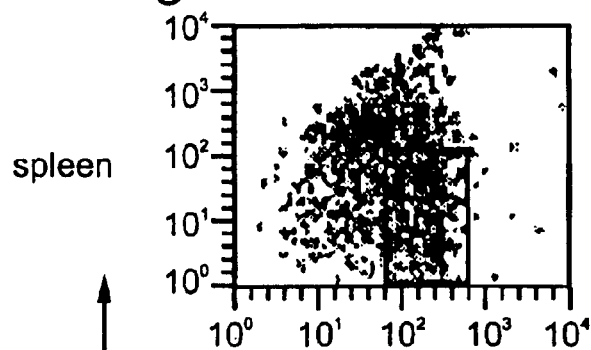
Figure 1F:
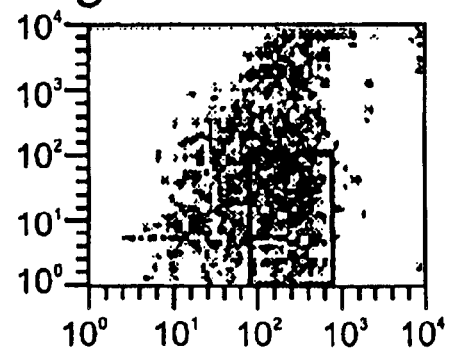
Figure 1H:
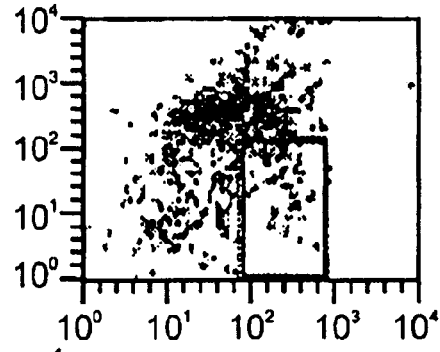
Figure 1H:
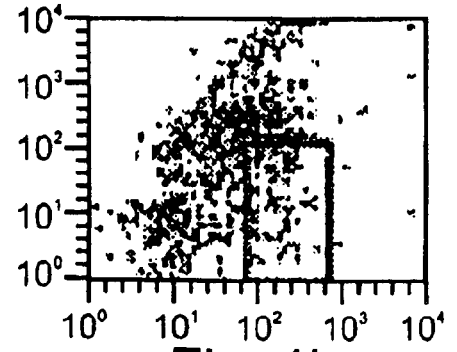

The present invention is of methods and compositions which can be used to treat an inflammation in a subject in need thereof. Specifically, the present invention employs ultra-low levels of IFN-γ to treat a range of diseases associated with, and/or accompanied by, inflammation such as, but not limited to, graft rejection, allergy, autoimmune disease and hypersensitivity.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or exemplified in the Examples. The invention is capable of other embodiments or of being practiced or carried out in various ways. Also, it is to be understood that the phraseology and terminology employed herein is for the purpose of description and should not be regarded as limiting.

Inflammatory processes, whether normal or pathological, require adhesion of lymphocytes to the ECM so as to enable their extravasation, migration and infiltration. Such processes are critical for the maturation, antigenic activation and effector responses of lymphocytes which, in turn, are required to mediate pro-inflammatory functions. One approach which has been attempted in the prior art to treat diseases associated with, and/or accompanied by, inflammation has been to employ high doses of the cytokine IFN-γ which, however was shown to lead to side-effects of unacceptable severity.

Various methods of employing IFN-γ to treat diseases associated with, and/or accompanied by, inflammation have been described by the prior art.

For example, as described in the Background section, prior art treatment of asthma in mice required administration of at least 800,000 units IFN-γ per kilogram body weight for effective suppression of disease.

Furthermore, in humans, as described in the Background section above, prior art treatment of the inflammatory diseases idiopathic pulmonary fibrosis and Crohn's disease was attempted with doses of 33,000 and 15,000 units of IFN-γ per kilogram body weight, respectively. Such high levels of IFN-γ, however, caused side-effects of such severity as to prohibit their use in humans.

Activity units of IFN-γ are titrated by manufacturers of this cytokine via an anti-viral activity assay wherein 1 unit/ml of interferon is defined as the concentration necessary to produce a cytopathic effect of 50% [Rubinstein, S., Familletti, P. C., and Pestka, S. (1981) "Convenient Assay for Interferons," J. Virol. 37, 755–758; Familletti, P. C., Rubinstein, S., and Pestka, S. (1981) "A Convenient and Rapid Cytopathic Effect Inhibition Assay for Interferon," in Methods in Enzymology, Vol. 78 (S. Pestka, ed.), Academic Press, New York, 387–394].

Thus, all prior art approaches employing IFN-γ have failed to provide adequate solutions for treating diseases associated with, and/or accompanied by, inflammation without risk of severe side-effects While conceiving the present invention it was hypothesized that suitably low doses of IFN-γ could be employed for effectively treating diseases associated with, and/or accompanied by, inflammation while being sufficiently low so as to avoid causing the prohibitively severe side-effects caused by prior art levels thereof.

While reducing the present invention to practice it was unexpectedly uncovered, as described in detail in Example 2 of the Examples section below, that levels of IFN-γ as low as 4 units per kilogram body weight (0.1 units IFN-γ administered systemically to a 25 g mouse) could be employed to effectively treat DTH, that levels of IFN-γ as low as 200 units per kilogram body weight (5 units IFN-γ administered systemically to a 25 g mouse) could be employed to effectively treat delayed-type hypersensitivity, allograft rejection and colitis and that levels of IFN-γ, as low as 240 units per kilogram body weight (6 units IFN-γ administered systemically to a 25 g mouse) could be employed to very effectively suppress asthma.

Hence, the method of the present invention can effectively treat a range of diseases associated with inflammation via levels of IFN-γ two to four orders of magnitude lower than the lowest levels employed in the prior art and, as such, the method of the present invention represents a radical improvement over the prior art.

Thus, according to one aspect of the present invention, there is provided a method of treating an inflammation in a subject in need thereof, which method is effected by administering to the subject ultra-low levels of IFN-γ, ultra-low levels of IFN-γ being defined herein as levels administered at 1–8000 units per kilogram body weight.

According to the present invention, IFN-γ is administered at levels such as, but not limited to, 1–8,000, 0.2–2,000, 0.5–1,000, 1–500, 2–240 and 4–240 units per kilogram body weight to treat diseases associated with, and/or accompanied by, inflammation.

According to a further aspect of the present invention, IFN-γ at such levels is administered in a pharmaceutical composition which is preferably packaged and identified for treatment of an inflammatory disease, disorder or condition.

According to a preferred embodiment of the present invention, the pharmaceutical composition includes a pharmaceutically acceptable carrier adapting the composition for local or systemic administration by a route such as, but not limited to, the intranasal, transdermal, intradermal, oral, buccal, parenteral, topical, rectal or inhalation routes.

Preferably, IFN-γ is administered via the parenteral route, such as, for example, via injection, as described below in Example 2 of the Examples section.

According to the method of the present invention, the pharmaceutically acceptable carrier consists of, for example, a solution, a suspension, an emulsion, a gel or a skin pad.

According to an embodiment of the present invention, the pharmaceutical composition further includes a formulating agent such as, but not limited to, a suspending agent, a stabilizing agent and a dispersing agent.

Preferably, the pharmaceutically acceptable carrier provides IFN-γ in solution.

According to a preferred embodiment of the present invention the pharmaceutically acceptable carrier is adapted for systemic or local administration.

Preferably, IFN-γ is administered systemically, as described in Example 2 of the Examples section, below.

Thus, according to a further aspect of the present invention, the dose-unit for systemic administration of the pharmaceutical composition of the present invention comprises, as an active ingredient, IFN-γ in an amount, such as, but not limited to, 1–800,000, 2–400,000, 5–200,000, 10–100,000, 25–50,000 and 60–21,600 units.

Preferably, the dose-unit for systemic administration of the pharmaceutical composition of the present invention comprises, as an active ingredient, IFN-γ in an amount of 60–21,600 units. Such a range covers a minimal dose corresponding to 4 units per kilogram in a 15 kilogram individual to a maximal dose corresponding to 240 units per kilogram in a 90 kilogram individual.

Alternately, the dose-unit for local administration of the pharmaceutical composition of the present invention comprises, as an active ingredient, IFN-γ in an amount, such as, but not limited to, 0.0002–8, 0.0005–8, 0.001–8, 0.002–8 and 0.004–8 units.

Preferably, the dose-unit for local administration of the pharmaceutical composition of the present invention comprises, as an active ingredient, IFN-γ in an amount of 0.004–8 units. Such a range covers a minimal local dose corresponding to a concentration of 4 units per kilogram bulk tissue in 1 cc of bulk tissue to a maximal local dose corresponding to a concentration of 240 units per kilogram bulk tissue in 100 cc of bulk tissue.

Thus, according still a further aspect of the present invention, the dose-unit of the pharmaceutical composition of the present invention achieves, upon administration, an IFN-γ bulk tissue concentration at a site of inflammation, such as, but not limited to, 1–8,000, 1.5–4,000, 2–2,000, 2.5–1,000, 3–500, 3.5–240 and 4–240 units per kilogram body weight.

Preferably, according to the method of the present invention, IFN-γ is administered so as to achieve a concentration of 4–240 units per kilogram body weight at a site of inflammation. The concentrations ranging between 4–240 units per kilogram body weight were determined, while reducing the present invention to practice, as being optimal for treatment of various diseases associated with, and/or accompanied by, inflammation, as described hereinabove and as described in further detail in Example 2 of the Examples section below.

According to the method of the present invention, treatment of an inflammation with IFN-γ is effected by administering IFN-γ at levels sufficiently low so as to avoid the severe side-effects associated with prior art administration of high levels of IFN-γ, as described hereinabove.

Examples of such unwanted side-effects include, but are not limited to, fever, chills, flu symptoms, bone pain, muscle pain, anorexia, fatigue, nausea, vomiting, leukopenia, diarrhea, fatigue, abnormal liver function, black, tarry stools; blood in urine, blood in stools, confusion, cough, hoarseness, loss of balance control, mask-like face, painful urination, difficult urination, pinpoint red spots on skin, shuffling walk, stiffness of arms, stiffness of legs, trembling of hands, shaking of hands, trembling of fingers, shaking of fingers, trouble in speaking, trouble in swallowing, trouble in thinking, trouble in concentrating, trouble in walking, unusual bleeding, unusual bruising, general feeling of discomfort, general feeling of illness, headache, skin rash, unusual tiredness, back pain, side-pain, dizziness, joint pain, loss of appetite and weight loss.

According to an embodiment of the present invention, IFN-γ is used to treat inflammation associated with inflammatory diseases, disorders or conditions.

Examples of inflammatory diseases include, but are not limited to, chronic inflammatory diseases and acute inflammatory diseases.

According to one preferred embodiment of the present invention IFN-γ is employed to treat chronic inflammatory disease, such as colitis, as described in Example 2 of the Examples section, below.

According to another preferred embodiment of the present invention, IFN-γ is employed to treat acute inflammatory disease, such as asthma, as described in Example 2 of the Examples section, below.

According to yet a further embodiment, IFN-γ is used to treat an inflammation associated with hypersensitivity.

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

According to one embodiment of the present invention, IFN-γ is employed to treat Type I or immediate hypersensitivity, such as asthma, as described hereinabove and as further described in Example 2 of the Examples section, below.

Examples of Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1–2):49), sclerosis, systemic sclerosis (Renaudineau Y. et al., Clin Diagn Lab Immunol. 1999 March; 6 (2):156); Chan O T. et al., Immunol Rev 1999 June;169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998;7 Suppl 2:S107–9), neurodegenerative diseases, neurological diseases, neurological autoimmune diseases, multiple sclerosis (Cross A H. et al., J Neuroimmunol 2001 Jan. 1; 112 (1–2):1), Alzheimer's disease (Oron L. et al., J Neural Transm Suppl. 1997; 49:77), myasthenia gravis (Infante A J. And Kraig E, Int Rev Immunol 1999; 18 (1–2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107–9), granulomatosis, Wegener's granulomatosis, arteritis, Takayasu's arteritis and Kawasaki syndrome (Praprotnik S. et al., Wien Klin Wochenschr 2000 Aug. 25; 112 (15–16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al, Am J Cardiol. 1999 Jun. 17; 83 (12A):75H), thrombocytopenic purpura (Moccia F. Ann Ital Med Int. 1999; April–June; 14 (2):114); hemolytic anemia, autoimmune hemolytic anemia (Efremov D G. et al., Leuk Lymphoma 1998 January; 28 (3–4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5–6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

According to a yet another embodiment, the method of the present invention is employed to treat Type IV or T lymphocyte mediated hypersensitivity.

Preferably, the method of the present invention is employed to treat Type IV or T lymphocyte mediated hypersensitivity such as DTH, as described hereinabove and as described in greater detail in Example 2 of the Examples section, below.

Examples of Type IV or T cell mediated hypersensitivity, include, but are not limited to, rheumatoid diseases, rheumatoid arthritis (Tisch R, McDevitt H O. Proc Natl Acad Sci USA Jan. 1994 Jan. 18; 91 (2):437), systemic diseases, systemic autoimmune diseases, systemic lupus erythematosus (Datta S K., Lupus 1998;7 (9):591), glandular diseases, glandular autoimmune diseases, pancreatic diseases, pancreatic autoimmune diseases. Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol March 1993;92 (1):77); ovarian diseases (Garza K M. et al., J Reprod Immunol February 1998;37 (2):87), prostatitis, autoimmune prostatitis (Alexander R B. et al., Urology December 1997; 50 (6):893), polyglandular syndrome, autoimmune polyglandular syndrome, Type I autoimmune polyglandular syndrome (Hara T. et al., Blood. Mar. 1, 1991; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March ; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

As described in Example 2 of the Examples section, below, administration of as little as 200 and 240 units IFN-γ per kilogram body weight, respectively, is used, according to the method of the present invention, to very effectively treat $T_h1$ and $T_h2$ lymphocyte mediated hypersensitivities, such as colitis and asthma.

According to a preferred embodiment of the present invention, IFN-γ is employed to treat an inflammation associated with an autoimmune disease.

Examples of autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

According to another preferred embodiment of the present invention, IFN-γ is employed to treat autoimmune gastrointestinal diseases, such as colitis, as described hereinabove and as described in further detail in Example 2 of the Examples section, below.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107–9), Wegener's granulomatosis, Takayasu's arteritis, Kawasaki syndrome (Praprotnik S. et al, Wien Klin Wochenschr 2000 Aug. 25; 112 (15–16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April–June; 14 (2):114; Semple J W. et al., Blood 1996 May 15; 87 (10):4245), autoimmune hemolytic anemia (Efremov D G. et al., Leuk Lymphoma 1998 January; 28 (3–4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl:S125), autoimmune thyroid diseases, Graves' disease (Orgiazzi J. Endocrinol Metab Clin North Am 2000 June; 29 (2):339; Sakata S. et al., Mol Cell Endocrinol 1993; 92 (1):77), spontaneous autoimmune thyroiditis (Braley-Mullen H. and Yu S, J Immunol December 2000; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan 1; 112 (1–2):1), Alzheimer's disease (Oron L. et al., J Neural Transm Suppl. 1997; 49:77), myasthenia gravis (Infante A J. And Kraig E, Int Rev Immunol 1999; 18 (1–2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units SA 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5–6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S 107–9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1–2):49) and systemic sclerosis (Renaudineau Y. et al., Clin Diagn Lab Immunol. 1999 March; 6 (2):156); Chan O T. et al., Immunol Rev 1999 Jun;169:107).

According to an embodiment of the method of the present invention, IFN-γ is employed to treat an inflammation associated with infectious diseases.

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

According to a preferred embodiment of the method of the present invention, IFN-γ is employed to treat an inflammation associated with a disease associated with transplantation of a graft, as described hereinabove and as described in further detail in Example 2 of the Examples section, below.

Examples of diseases associated with transplantation of a graft include, but are not limited to, graft rejection, chronic graft rejection, subacute graft rejection, hyperacute graft rejection, acute graft rejection and graft versus host disease.

Types of grafts whose rejection can be treated by the method of the present invention include, but are not limited to, syngeneic grafts, allografts and xenografts.

According to a preferred embodiment of the present invention, IFN-γ is employed to treat allograft rejection, as described in further detail in Example 2 of the Examples section, below.

Examples of grafts include cellular grafts, tissue grafts, organ grafts and appendage grafts.

Examples of cellular grafts include, but are not limited to, stem cell grafts, progenitor cell grafts, hematopoietic cell grafts, embryonic cell grafts and a nerve cell grafts.

Examples of tissue grafts include, but are not limited to, skin grafts, bone grafts, nerve grafts, intestine grafts, corneal grafts, cartilage grafts, cardiac tissue grafts, cardiac valve grafts, dental grafts, hair follicle grafts and muscle grafts.

Examples of organ grafts include, but are not limited to, kidney grafts, heart grafts, skin grafts, liver grafts, pancreatic grafts, lung grafts and intestine grafts.

Examples of appendage grafts include, but are not limited to, arm grafts, leg grafts, hand grafts, foot grafts, finger grafts, toe grafts and sexual organ grafts.

According to a preferred embodiment of the present invention, IFN-γ is employed to treat kidney allograft rejection, as described hereinabove and in detail in Example 2 of the Examples section, below.

According to a preferred embodiment of the method of the present invention, IFN-γ is employed to treat inflammation associated with allergic diseases, as described hereinabove and as described in greater detail in Example 2 of the Examples section, below.

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Preferably, IFN-γ is employed, according to the method of the present invention, to treat asthma, as described hereinabove and as described in greater detail in Example 2 of the Examples section, below.

According to an embodiment of the method of the present invention, IFN-γ is employed to treat inflammations associated with neurodegenerative diseases.

According to another embodiment of the method of the present invention, IFN-γ is employed to treat inflammations associated with cardiovascular diseases.

According to another preferred embodiment of the method of the present invention, IFN-γ is employed to treat inflammations associated with gastrointestinal diseases, as described hereinabove and as described in greater detail in Example 2 of the Examples section, below.

Examples of gastrointestinal diseases include, but are not limited to, the examples of antibody-mediated gastrointestinal diseases listed hereinabove, the examples of T lymphocyte-mediated gastrointestinal diseases listed hereinabove, the examples of autoimmune gastrointestinal diseases listed hereinabove and hemorrhoids.

According to yet another preferred embodiment of the method of the present invention, IFN-γ is employed to treat colitis, as described hereinabove and as described in greater detail in Example 2 of the Examples section, below.

According to still another embodiment of the method of the present invention, IFN-γ is employed to treat inflammations associated with neurodegenerative diseases.

According to a further embodiment of the method of the present invention, IFN-γ is employed to treat inflammations associated with tumors.

Examples of tumors include, but are not limited to, malignant tumors, benign tumors, solid tumors, metastatic tumors and non-solid tumors.

According to a embodiment of the method of the present invention, IFN-γ is employed to treat inflammation associated with septic shock.

According to another embodiment of the method of the present invention, IFN-γ is employed to treat inflammation associated with anaphylactic shock.

According to yet another embodiment of the method of the present invention, IFN-γ is employed to treat inflammation associated with toxic shock syndrome.

According to still another embodiment of the method of the present invention, IFN-γ is employed to treat inflammation associated with cachexia.

According to a further embodiment of the method of the present invention, IFN-γ is employed to treat inflammation associated with necrosis.

According to still a further embodiment of the method of the present invention, IFN-γ is employed to treat inflammation associated with gangrene.

According to yet a further embodiment of the method of the present invention, IFN-γ is employed to treat inflammations associated with prosthetic implants.

Examples of prosthetic implants include, but are not limited to, breast implants, silicone implants, dental implants, penile implants, cardiac implants, artificial joints, bone fracture repair devices, bone replacement implants, drug delivery implants, catheters, pacemakers, respirator tubes and stents.

According to a further embodiment of the method of the present invention, IFN-γ is employed to treat inflammation associated with menstruation.

According to still a further embodiment of the method of the present invention, IFN-γ is employed to treat inflammations associated with ulcers.

Examples of ulcers include, but-are not limited to, skin ulcers, bed sores, gastric ulcers, peptic ulcers, buccal ulcers, nasopharyngeal ulcers, esophageal ulcers, duodenal ulcers, ulcerative colitis and gastrointestinal ulcers.

According to yet a further embodiment of the method of the present invention, IFN-γ is employed to treat inflammations associated with injuries.

Examples of injuries include, but are not limited to, abrasions, bruises, cuts, puncture wounds, lacerations, impact wounds, concussions, contusions, thermal burns, frostbite, chemical burns, sunburns, dessications, radiation burns, radioactivity burns, smoke inhalation, torn muscles, pulled muscles, torn tendons, pulled tendons, pulled ligaments, torn ligaments, hyperextensions, torn cartilage, bone fractures, pinched nerves and a gunshot wounds.

According to an embodiment of the method of the present invention, IFN-γ is employed to treat musculo-skeletal inflammations.

Examples of musculo-skeletal inflammations include, but are not limited to, muscle inflammations, myositis, tendon inflammations, tendinitis, ligament inflammations, cartilage inflammation, joint inflammations, synovial inflammations, carpal tunnel syndrome and bone inflammations.

According to an embodiment of the method of the present invention, IFN-γ is employed to treat idiopathic inflammations.

According to another embodiment of the method of the present invention, IFN-γ is employed to treat inflammations of unknown etiology.

It is expected that during the life of this patent many relevant medical diagnostic techniques will be developed and the scope of the term analytic mechanism is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I—III Coligan J. E., ed. (1994); Stites et al. (eds), "Basic and Clinical Immunology" (8$^{th}$ Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Ultra-Low Levels of IFN-γ Inhibit B Cell Adhesion to Extracellular Matrix and Homing to Lymph Nodes Inflammation mediated by lymphocytes, such as B lymphocytes, as described above, plays a major role in the pathogenesis of many diseases, such as, but not limited to, autoimmune diseases, allergy, graft rejection, bacterial and viral infections and cancer. Since B lymphocytes play a central role in humoral and cellular immunity via antibody production and antigen presentation, respectively, the ability to downregulate B cell function is a highly desired therapeutic goal. Such downregulation may be effected, for example, by downregulation of B cell adhesion to ECM and homing to LNs, so as to interfere with extravasation and hence activation of B cells and their migration to sites of pathogenesis. Since immature B cells are negatively selected in the bone marrow and in the periphery before their maturation in the spleen via apoptotic elimination in response to self-antigen, natural mechanisms exist preventing the entry of immature B cells into non-splenic sites of foreign antigen-presentation such as LNs so as to prevent apoptosis of foreign antigen-specific clones. As demonstrated in the experiments elaborated below, prevention of immature B cell migration into LNs is mediated by autocrine effects of ultra-low levels of IFN-γ, at least partly via inhibition of adhesion of activated cells to ECM. The experiments described below in this Example further demonstrate the ability of such ultra-low levels of IFN-γ to prevent adhesion of B lymphocytes to ECM and migration to LNs by activated mature B cells.

The method of the present invention therefore, harnesses these demonstrated anti-inflammatory properties of ultra-low levels of IFN-γ to treat inflammation-related diseases, disorders or conditions whose pathogenesis involves B lymphocytes. Such therapeutic uses of ultra-low levels of IFN-γ represent an improvement over prior art therapeutic uses of IFN-γ since, as described above, such prior art approaches employed high doses of IFN-γ producing an unacceptable incidence of undesirable side-effects.

Materials and Methods:

Cells: Cells were obtained from 6–8 week-old C57BL/6 or C57BL/6J-derived invariant chain deficient (Ii$^{-/-}$)

(Elliott, E. A. et al., J. Exp. Med. 1994, 179:681) or IFN-γ deficient (IFN-γ$^{-/-}$) mice. Splenocytes and LN cells were purified as previously described (Elliott, E. A. et al., J. Exp. Med. 1994, 179:681).

Purification of B cells: B cells were purified by treating splenocyte suspensions with anti-Thy1.2, -CD4 and -CD8 antibodies (Southern Biotechnology Associates, USA) followed by treatment with Low Tox-M complement (Cedarlane, Canada). To separate IgD$^-$ from IgD$^+$ cells the MACS system (Miltenyi Biotec, Auburn Calif.) was employed. The IgD$^-$ population was incubated with anti-CD45R (B220) antibody-conjugated magnetic beads and re-separated using the MACS system. For comparison of populations, immature Ii$^{-/-}$ B cells were purified by MACS and CD45R beads. T cells were obtained by collecting the B220$^-$ population. To separate IgD$^-$ CD21$^+$ from IgD$^-$ CD21$^-$ cells, IgD$^-$ cells were separated according to CD21 expression using the MACS system. The IgD$^-$ CD21$^-$ cells were incubated with anti-CD45R magnetic beads and re-separated. The purity of each cell population was determined by flow cytometry.

Immunofluorescence analysis reagents: The following antibodies (Pharmingen) were employed: RA3-6B2 anti-CD45R, B3b4 anti-CD23, 7G6 anti-CD21/CD35, R6-60.2 anti-IgM, AMS 9.1 anti-IgD, 7G6 anti-CD21/CD35, MEL-14 anti-L-selectin, R1–2 anti-VLA-4, 5H10–27 anti-VLA-5, 2D7 anti-LFA-1 and 9C10 anti-CD49d (anti-α4).

Adhesion assays: Adhesion assays were performed as previously described (Gilat, D. et al., J Immunol. 1994, 153:4899). Briefly, 96-well plates were coated with FN (100 μg/ml). Cells labelled with $^{51}$Cr were suspended in RPMI supplemented with 0.1% FCS or conditioned medium collected from control or Ii$^{-/-}$ cells. The cells were plated at 2×10$^5$ cells per coated well in the presence or absence of LPS (10 μg/ml), PMA (0.25 μg/ml), IL-2 (0.2 units/μl), SDF-1 (1 μg/ml), EDTA (5 mM) or combined LDV and RGD peptides (800 μg/ml each). After 30 min the plates were washed, adherent cells were lysed and the released radioactivity was determined. Results were expressed as the mean percentage (±SD) of bound cells from quadruplicate wells. The percentage of adherent cells was calculated as follows: (# residual cells/well)÷(total # cells added/well)×100.

RNA isolation and reverse transcription: Total RNA was isolated from cells using the Tri Reagent kit (Molecular Research Center, Cincinnati, Ohio). Reverse transcription was carried out using Superscript II RT (Gibco BRL, USA). The primers and PCR conditions employed have been previously described (Reiner, S. L. et al., J. Immunol. Methods 1994, 175:275).

Detection of IFN-γ: Cells were lysed as described previously (Elliott, E. A. et al., J. Exp. Med. 1994, 179:681). Interferon-γ was immunoprecipitated by overnight incubation with anti-IFN-γ monoclonal antibody (R4-6A2) (Pharmingen, USA) followed by incubation with protein-G Sepharose beads (Pharmacia, Sweden). Crude cell lysate proteins or immunoprecipitated proteins were separated by 12% (w/v) SDS-PAGE. Separated proteins were electroblotted onto nitrocellulose and probed with anti-IFN-γ antibody (R4-6A2) followed by horseradish peroxidase-conjugated goat anti-rat IgG antibody (Jackson ImmunoResearch).

Tracking of cells in vivo: Cells were incubated for 30 min with various treatments. The cells were then washed and labelled for 30 min with the fluorescent marker BCECF-AM (10 μg/ml) (Molecular Probes) with an efficiency of approximately 97%. Aliquots of 5×10$^7$ washed cells were injected intravenously into pairs of C57BL/6 mice. After 3.5 h, spleen and LNs were removed and the percentages of fluorescent cells in both organs were analyzed by immunofluorescent flow cytometry. Percent inhibition of cell migration was calculated as: 100%−[(no. of cells in treated mice)÷(no. of cells in control mice)×100]. Results presented are the average of three different experiments.

Laminar flow assays: Polystyrene plates were coated with FN (30 μg/ml; Sigma, Israel) in the presence or absence of SDF-1 (0.5 μg/ml). These plates were assembled to form the lower wall in a parallel wall flow chamber tube, as previously described (Lawrence, M. B. et al., Eur. J. Immunol. 1995, 25:1025). Cells were allowed to settle in the coated capillary tube for 2 min before being subjected to increasing laminar flow. Cell adhesion under flow conditions was videotaped for subsequent manual quantitation.

Cytokine concentrations: Cytokines (Gibco-BRL), were employed in adhesion assays at the following concentrations: IL-4 (10$^3$ units/ml), IL-5 (16 units/ml), IL-6 (16 units/ml), IL-12 (3.5 ng/ml) and IFN-γ (0.1 unit/ml).

Experimental Results:

Immature B cells are excluded from the LNs: To determine whether immature B cells are indeed excluded from secondary lymphoid organs while recirculating through the body, profiles of B cell distribution in spleen and LNs in control and in Ii$^{-/-}$ mice were analyzed.

In Ii$^{-/-}$ mice there was a striking decrease in the proportion of B cells populating the LN relative to wild-type mice (FIGS. 1a–d and Table 1). Furthermore B cells in Ii$^{-/-}$ mice were found to be arrested at an immature stage, as characterized by low levels of surface IgD (FIGS. 1e–j and Table 1) and partial CD21 surface expression (FIGS. 1i–j), as previously described (Shachar, I., and R. A. Flavell. Science 1996, 274:106; Kenty, G. et al., J. Immunol. 1998, 160:606; Kenty, G., and E. K. Bikoff. J. Immunol. 1999, 163:232).

TABLE 1

Total spleen cell number and percentages of the B cell population, the mature (IgD$^+$) and the immature (IgD$^-$) subpopulations in control and Ii$^{-/-}$ mice.

| | Cells | Control | Ii$^{-/-}$ |
|---|---|---|---|
| Spleen | Total | (9.3 ± 2) × 10$^7$ | (6 ± 1.6) × 10$^7$ |
| | % B | 46.5 ± 8.2 | 47 ± 10.2 |
| | % IgD$^+$ | 39.5 | 2.2 ± 1 |
| | % IgD$^-$ | 6.8 | 44.5 |
| LN | % B | 36 ± 3 | 15 ± 4 |
| | % IgD$^+$ | 35 | 13.3 |
| | % IgD$^-$ | 1 | 1.6 |

These observations confirm that immature B cells are depleted from the LN, even though the Ii$^{-/-}$ population was found to express significant surface levels of the endothelial adhesion molecule L-selectin (FIGS. 1k–l).

Unlike mature B cells, activated B cells displaying an immature phenotype do not adhere to ECM: To migrate to the LNs, leukocytes, such as B cells, must interact with adhesive components of the ECM (Butcher, E. C., and L. J. Picker. Science 1996, 272:60). Therefore the adhesion response of activated mature (control) and immature (Ii$^{-/-}$) B splenocytes was compared by studying their ability to adhere to FN, a major ECM-based integrin ligand, as follows.

Cells labelled with $^{51}$Cr were plated for 30 min on FN-coated microtiter wells in the presence of the cell activator PMA, a potent agonist of integrin-mediated adhesion (Shimizu, Y. et al., J. Exp. Med. 1992, 175:577; Faull, R. J. et al., J. Exp. Med. 1994, 179:1307), LPS, a B cell mitogen, or SDF-1, a potent B cell chemoattractant (Bleul, C. C. et al., J. Exp. Med. 1998, 187 187:753) and adhesion was assessed.

Figure 2A:
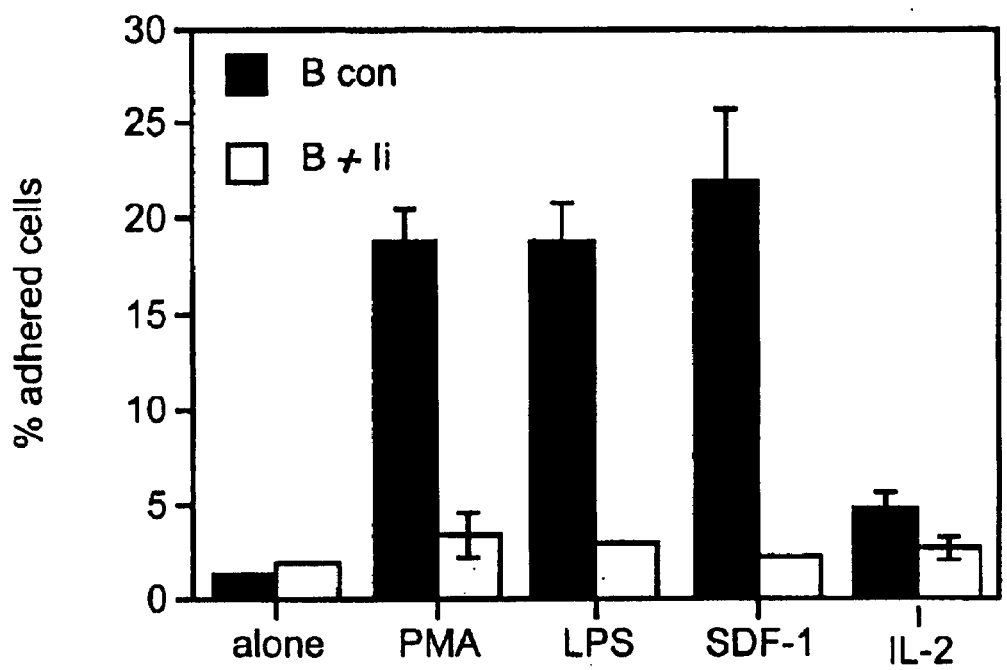
FIG. 2a is a histogram depicting the percentage of wild-type mature B cells (B con) or immature B cells from Ii$^{-/-}$ mice (B Ii$^{-/-}$) adhering to FN in the presence of PMA, LPS, SDF-1, or IL-2 stimulation. One representative experiment out of five is depicted.
Figure 2B:
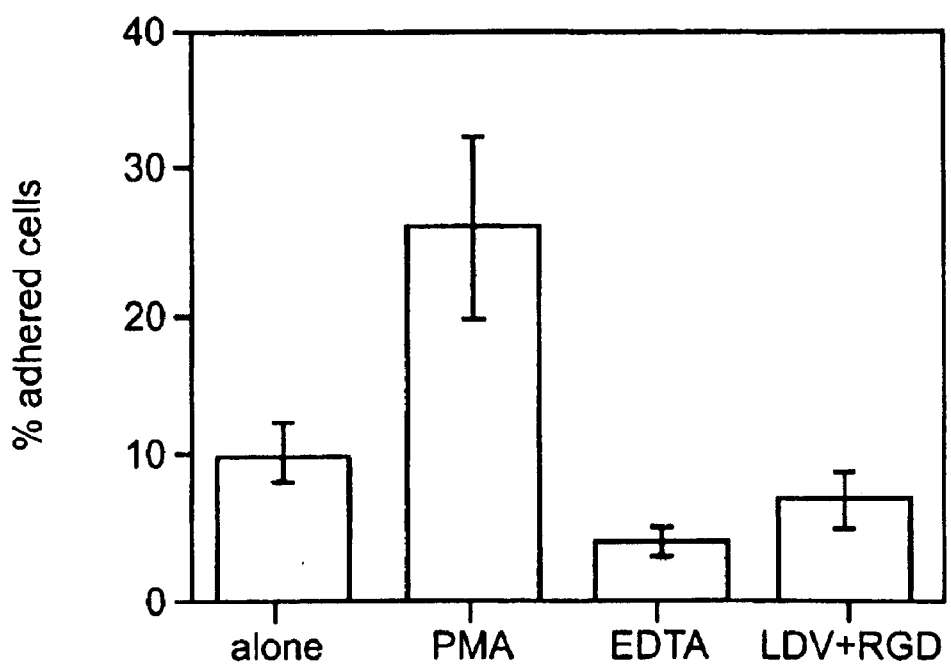
FIG. 2b is a histogram depicting percentage of control B cells adhering to fibronectin (FN) in the presence of PMA (0.2 μg/ml), EDTA (5 mM) or combined LDV and RGD peptides (800 μg/ml each).

Following stimulation, control B cells were found to dramatically increase their adhesion to FN, whereas in contrast, the adhesion of $Ii^{-/-}$ B cells remained unchanged (FIG. 2a). As expected, B cells did not respond to stimulation with IL-2. The adhesion of B lymphocytes to FN in response to stimulation was observed to be abrogated in the presence of the integrin-inhibitor EDTA, as well as by combined LDV and RGD peptides, selective blockers of VLA-4 and VLA-5 integrins (FIG. 2b). Thus, the observed adhesion response was integrin-mediated.

In order to determine whether the inability of $Ii^{-/-}$ B cells to increase adhesion to FN was due to the developmental stage of the cells or to Ii deficiency, the adherence of purified control $IgD^-$ and $Ii^{-/-}$ B cells in response to SDF-1 or PMA stimulation was compared. Like B cells derived from $Ii^{-/31}$ mice, $IgD^-$ B cells from control mice were unable to increase their adhesion to FN in response to stimulation (FIG. 2c). Thus, the stage of maturity, and not the lack of Ii, determined the response. Similar cell surface expression levels of the integrins VLA-4, VLA-5, LFA-1 and α4, the major FN receptors, were detected on both $Ii^{-/-}$ and control B cells (FIGS. 2d, 2e, 2f and 2g, respectively). Thus, immature B cells do not adhere to the ECM even though they possess the adhesive molecules required for such adherence.

Figure 2H:
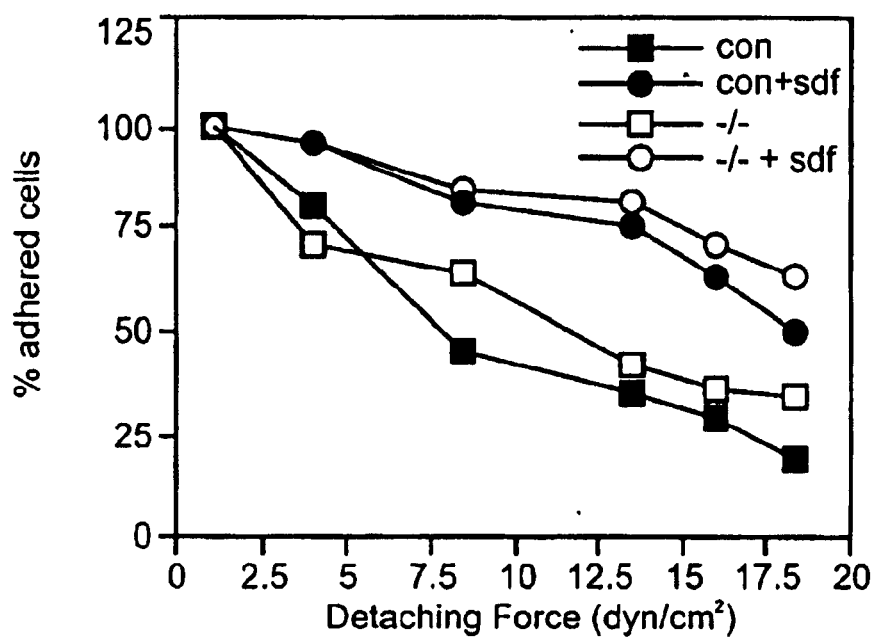
FIG. 2h is a plot depicting resistance to shear stress by mature and immature B cells adhering to FN in a short-term adhesion assay. Control (con) and Ii$^{-/-}$ B cells were allowed to attach to plastic tissue culture dishes coated with FN, alone or co-immobilized with SDF-1 (sdf). Following attachment, flow was initiated and increased in 2- to 2.5-fold increments every 10 s. The number of cells remaining bound at each interval was determined and is expressed as the percentage of input cells remaining bound. One representative experiment out of three is depicted.

To verify that intrinsic integrin function was not impaired, both control and $Ii^{-/-}$ populations were tested in a short-term adhesion assay on FN-coated surfaces assembled in a flow chamber apparatus. In the absence of stimulation, $Ii^{-/-}$ B cells were shown to exhibit a slightly stronger spontaneous adhesion to FN than that of the control cells. Surprisingly, rapid adhesion stimulation to FN was induced in both cell types by a 2 min treatment with SDF-1 (FIG. 2h) or PMA (not shown).

These results indicated that both the expression of integrin receptors for FN and their ability to respond to rapid stimulation are normal in immature B cells. Thus, the lack of adhesion by immature cells during the 30 min adhesion assay appeared to result from inhibitory events subsequent to a normal initial integrin-mediated adhesion.

Figure 3A:
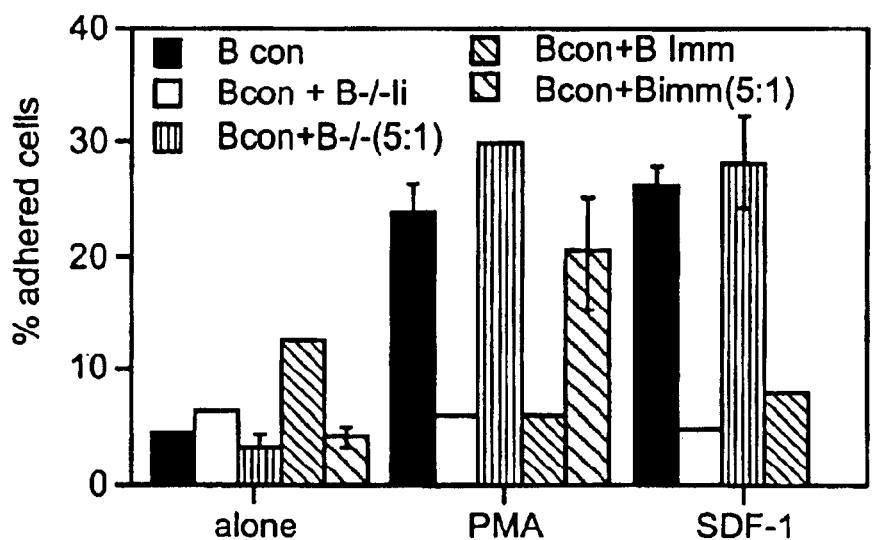
FIG. 3a is a histogram depicting the percentage of mature B cells adhering to FN-coated plastic tissue culture dishes in the presence of immature IgD$^-$ B cells from Ii$^{-/-}$ mice mixed at different ratios in the presence or absence of stimulation. Mature B cells (B con) were incubated with or without labelled immature IgD$^-$ B cells from Ii$^{-/-}$ (B Ii$^{-/-}$) or control (B imm) mice in a 1:1 (unless otherwise indicated) or 5:1 ratio in the presence or absence of stimulation.

B cells displaying an immature phenotype prevent ECM adhesion of co-mixed mature B cells: To test whether the inhibition of adhesion mediated by immature cells is transferable to other cells, the ability of purified control immature $IgD^-$ or $Ii^{-/-}$ B cells to inhibit the adhesion of purified mature $IgD^+$ B cells when co-mixed was analyzed. Both the control $IgD^-$ and the $Ii^{-/-}$ immature B cells were found to have an inhibitory effect on the adhesion of mature B-lymphocytes to FN when co-mixed in a 1:1 ratio (FIG. 3a). This inhibition could be abrogated by a five-fold dilution of the immature cells within the mature population.

B cells displaying an immature phenotype secrete a soluble factor preventing adhesion of mature B cells to ECM: To determine whether B cells displaying an immature phenotype inhibit adhesion mature B cell via a secreted factor, the activity of conditioned medium collected from B cells displaying an immature phenotype was analyzed for such inhibitory activity, as follows.

Figure 3B:
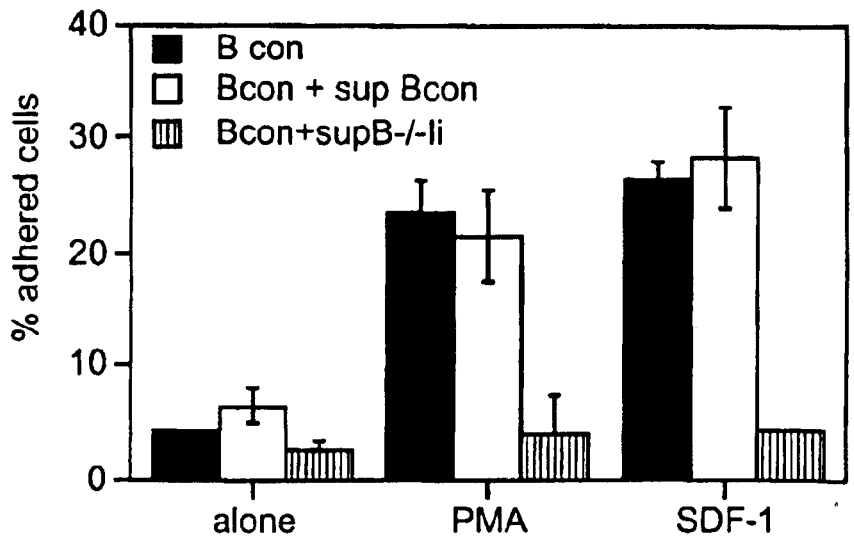
FIG. 3b is a histogram depicting the percentage of control B cells adhering to FN-coated plastic tissue culture dishes in the presence of conditioned medium (sup) collected from control (B con) or Ii$^{-/-}$ (B Ii$^{-/-}$) B cells in the presence or absence of stimulation. One representative experiment out of 7 is depicted.
Figure 3C:
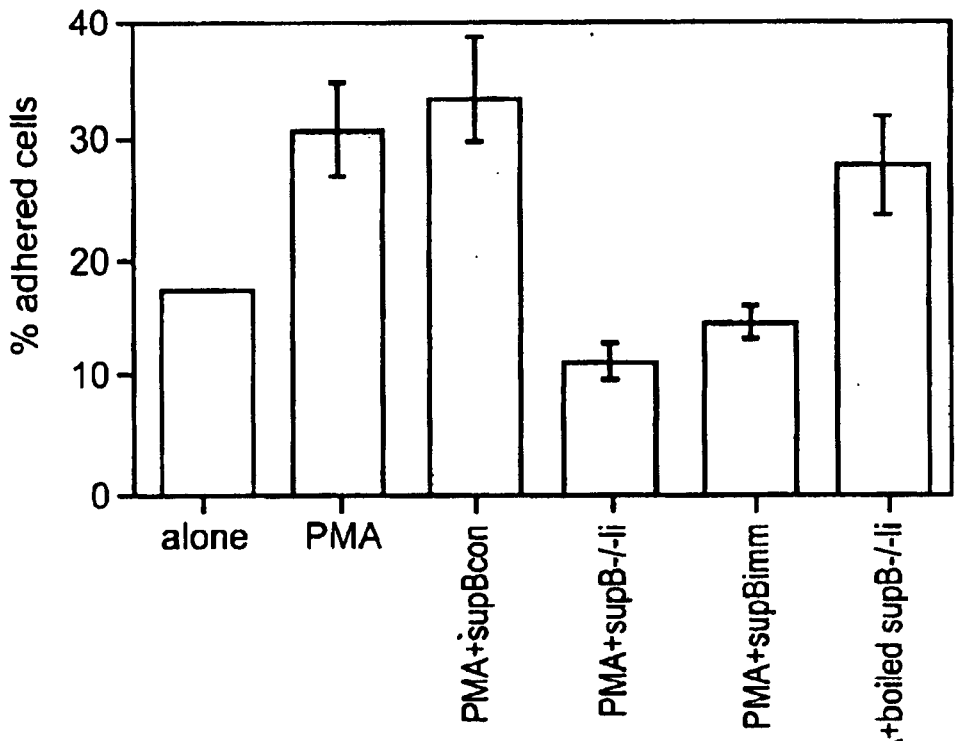
FIG. 3c is a histogram depicting the percentage of PMA-stimulated control B cells adhering to FN-coated plastic tissue culture dishes in the presence of conditioned medium (sup) collected from control B cells (B con), unboiled or boiled Ii$^{-/-}$ B (B Ii$^{-/-}$) or immature IgD$^-$ control B cells.

Control $IgD^-$ or $Ii^{-/-}$ B cells were plated in FN-coated microwells for 30 min and the conditioned medium was collected and tested for its ability to inhibit the adhesion of activated control B cells to FN. Whereas control B cell-conditioned medium was found not to affect cell adhesion, the adhesion response of cells incubated with $Ii^{-/-}$ B cell-conditioned medium (FIGS. 3b–c) or control $IgD^-$ B cell-conditioned medium (FIG. 3c) was inhibited following stimulation. Thus, immature B cell-conditioned medium was found to contain a soluble factor(s) inhibiting the adhesion of mature B cells. This factor(s) was furthermore determined to be heat sensitive (FIG. 3c).

Figure 4A:
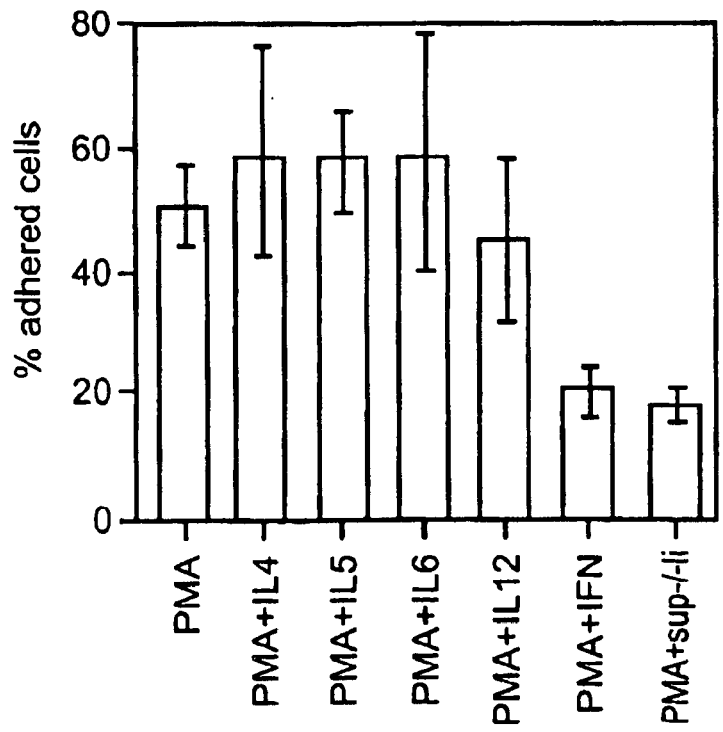
FIG. 4a is a histogram depicting the percentage of PMA-stimulated mature B cells adhering to FN-coated plastic tissue culture dishes in the presence of various cytokines or in the presence of immature B cell-conditioned medium.
Figure 4B:
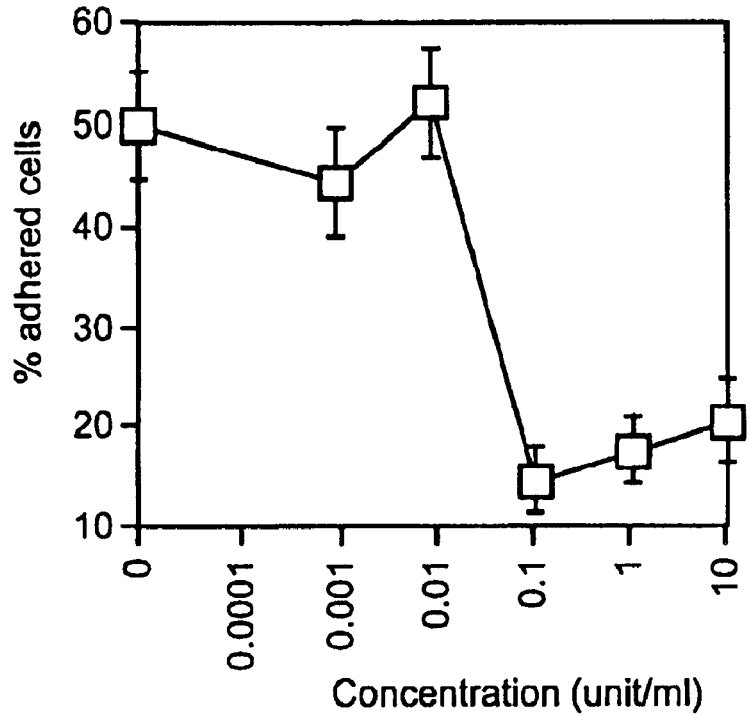
FIG. 4b is a plot depicting the percentage of PMA-stimulated mature B cells adhering to FN-coated plastic tissue culture dishes in the presence of different concentrations of recombinant IFN-γ.
Figure 4C:
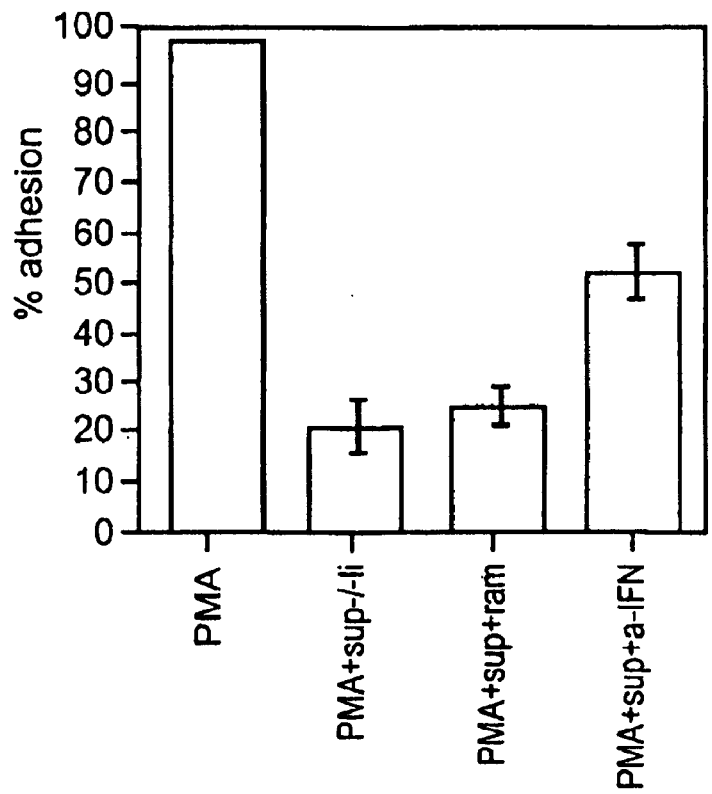
FIG. 4c is a histogram depicting the percentage of PMA-stimulated mature B cells adhering to FN-coated plastic tissue culture dishes in the presence of conditioned medium (sup) collected from Ii$^{-/-}$ B cells, with or without overnight treatment with rat anti-mouse IgG (ram) or rat anti-IFN-γ (a-IFN) antibody. Adhesion of cells stimulated with PMA only was designated as 100%.

Ultra-low levels of IFN-γ prevent adhesion of B cells to FN: To determine the identity of the soluble factor(s), various cytokines were screened for their ability to suppress adhesion of activated B cells to FN. Of the chemokines tested, only IFN-γ, optimally at ultra-low levels (0.1 unit/ml), was observed to mimic the effect of immature B cell-conditioned medium (FIG. 4a). Such effect was shown to be mediated in a concentration dependent manner (FIG. 4b). Neutralizing anti-IFN-γ antibody was demonstrated to substantially block such an inhibitory effect thereby confirming the capacity of IFN-γ to inhibit adhesion of activated B cells to the ECM (FIG. 4c).

Figure 4D:
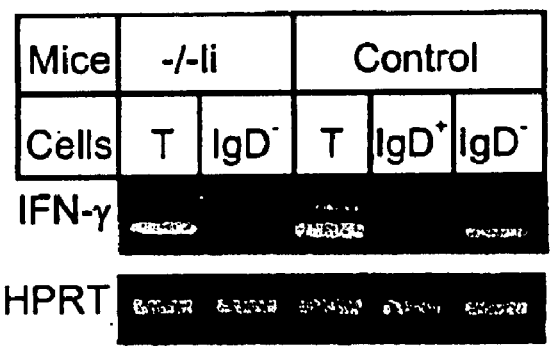
FIG. 4d depicts RT-PCR analysis of IFN-γ transcription in IgD$^-$ B cells of Ii$^{-/-}$ control mice and in IgD$^+$ B cells of control mice.

IFN-γ is selectively expressed in B cells displaying an immature phenotype: RT-PCR analysis revealed that IFN-γ expression by immature B cells is developmentally regulated at the transcriptional level. Whereas IFN-γ mRNA was detected in both control $IgD^-$ and $Ii^{-/-}$ B cells, this transcript was not found to transcribed in control $IgD^+$ B cells (FIG. 4d). Furthermore, the low frequency, partially mature $IgD^+$ B cell population present in $Ii^{-/-}$ mice was found to downregulate IFN-γ mRNA levels as well (data not shown).

In splenic lymphoid follicles, newly immigrant immature B cells can be separated from marginal zone cells by differential expression of the CD21 marker, thus in order to determine whether these populations display distinct IFN-γ expression profiles, transcription of IFN-γ in CD21 positive and negative $IgD^-$ populations was analyzed.

Figures 4E, 4F:
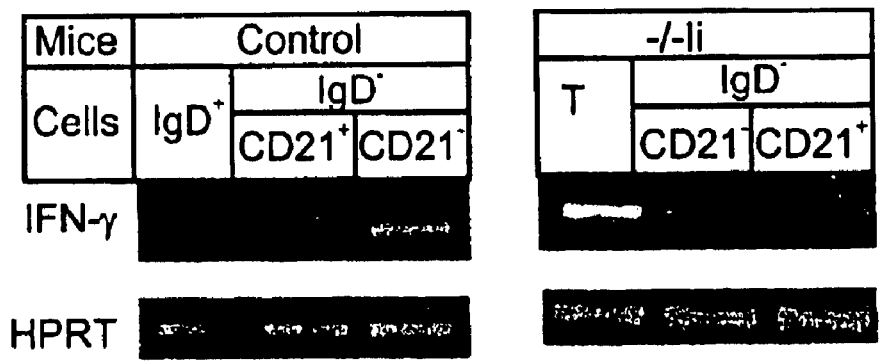
FIG. 4e depicts RT-PCR analysis of IFN-γ transcription in IgD$^+$, IgD$^-$ CD21$^+$ and IgD$^-$ CD21$^-$ B cells of control mice.
FIG. 4f depicts RT-PCR analysis of IFN-γ transcription in IgD$^-$ CD21$^-$ and IgD$^+$ CD21$^-$ B cells of Ii$^{-/-}$ mice.

As can be seen in FIGS. 4e and 4f, respectively, IFN-γ mRNA can be detected in the $IgD^-CD21^-$ cells of both control and $Ii^{-/-}$ mice. Thus, B cells downregulate IFN-γ transcription following acquisition of CD21, indicating that IFN-γ transcription is transcribed in immature B cells newly arrived in the spleen.

Figure 4G:
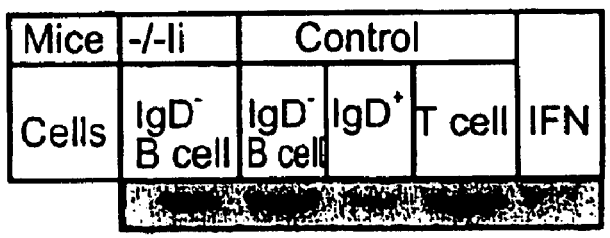
FIG. 4g depicts IFN-γ protein expression in total cell lysates of IgD$^-$ B cells from Ii$^{-/-}$ or control mice and IgD$^+$ B cells from control mice. The band representing IFN-γ is indicated.
Figure 4H:
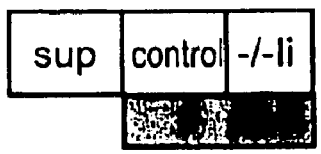
FIG. 4h depicts IFN-γ protein immunoprecipitated from conditioned medium (sup) of control and Ii$^{-/-}$ B cells. The protein species corresponding to IFN-γ is indicated.

Western immunoblotting analysis of IFN-γ protein expression in B cells during maturation revealed maturation-dependent regulation of IFN-γ production and secretion. Immature ($IgD^-$) B cells of control or $Ii^{-/-}$ mice were found to express significantly higher levels of IFN-γ protein than $IgD^+$ cells (FIG. 4g). Importantly, $Ii^{-/-}$ cell-conditioned medium was found to contain significant levels of IFN-γ protein, indicating that IFN-γ is both produced and secreted by immature B cells (FIG. 4h).

These results therefore demonstrated that IFN-γ is selectively transcribed, translated and secreted by B cells displaying an immature phenotype.

Ultra-low levels of IFN-γ inhibit migration of B cells to LNs: The effects of immature B cell-conditioned medium or ultra-low levels of IFN-γ on migration of normal B cells into LNs in vivo were investigated.

Bulk splenocytes of control or $Ii^{-/-}$ mice were treated with non-conditioned, control B cell-conditioned, $Ii^{-/-}$ B cell-conditioned medium, $Ii^{-/-}$ B cell-conditioned medium treated with anti-IFN-γ antibody or ultra-low levels of IFN-γ (1 unit/ml). Treated cells were washed, labelled with the fluorescent dye BCECF-AM and equal numbers of live cells were injected intravenously into control mice. The proportion of labelled cells recovered in the spleen and LNs was determined 3.5 h following injection.

The results obtained are depicted in FIG. 5a. The extent of labelled cell accumulation in the spleen was found to be unaffected by the various pre-treatments. In contrast, migration of $Ii^{-/-}$ and of control cells treated with $Ii^{-/-}$ B cell-conditioned medium or ultra-low levels of IFN-γ (1 unit/ml) to the LN was observed to be significantly decreased, whereas cells treated with control B cell-conditioned medium or non-conditioned medium, exhibited a degree of migration similar to untreated cells. Furthermore, when control cells were incubated in $Ii^{-/-}$ B cell-conditioned medium in the presence of neutralizing anti-IFN-γ antibody, the ability of this medium to inhibit homing of the cells to the LNs was substantially inhibited, thus confirming that the inhibitory effect of immature B cell-conditioned medium on homing of B cells to LNs is mediated by IFN-γ.

In order to confirm the biological significance of these results, the maturation profiles of B cells in spleen and LN of IFN-$\gamma^{-/-}$ mice were analyzed. While spleens of both types of mice were found to contain similar proportions of immature and mature B cells (FIGS. 5b and 5c, respectively), LNs of IFN-$\gamma^{-/-}$ mice were found to be populated with a significantly greater proportion of immature B cells than control B cells (FIGS. 5e and 5d, respectively). These results therefore indicated a physiological role for IFN-γ in preventing retention of immature B cells in secondary lymphoid organs, such as LNs.

In summary, these experiments demonstrated the ability of $Ii^{-/-}$ B cell-conditioned medium or ultra-low levels of IFN-γ to inhibit ECM adhesion and LN migration of B cells. Such capacity of ultra-low levels of IFN-γ to inhibit B cell functionality therefore demonstrates the effectiveness of the method of the present invention to treat inflammation-related disorders whose pathogenesis involves B lymphocytes. Therapeutic use of ultra-low levels of IFN-γ, according to the method of the present invention, represents a marked improvement over prior art therapeutic use of IFN-γ, employing high levels of this cytokine having been shown to produce an unacceptable incidence of side-effects.

Example 2

Ultra-Low Levels of IFN-γ Inhibit ECM Adhesion and Migration of T Lymphocytes and Constitute an Effective Treatment for T Cell-Mediated Diseases Immunoreactivity mediated by T lymphocytes, as described above, plays a major role in the pathogenesis of many diseases, such as autoimmune diseases, allergy, graft rejection, infection and cancer. This is a consequence of the fact that T lymphocytes are the major effectors of specific cellular immunity, both in their ability to respond to target cells expressing MHC-peptide complexes and in their ability to provide helper cytokines promoting B and T lymphocyte function. Thus, the ability to inhibit T lymphocyte function is a highly desired therapeutic goal.

As demonstrated in Example 1 with respect to B lymphocytes, inhibition of T lymphocyte effector functions can also be efficiently achieved by downregulating their capacity to adhere to ECM and to migrate. Such inhibition represents an effective means of preventing T lymphocyte migration to secondary lymphoid organs and inflamed tissues thereby respectively preventing activation of T lymphocytes by professional antigen-presenting cells and the triggering of effector function by target cells expressing foreign antigens in sites of inflammation.

Thus, experiments were performed, as described below, testing, and clearly demonstrating, the ability of ultra-low levels of IFN-γ to prevent ECM adhesion and migration to secondary lymphoid organ tissue by T lymphocytes, as well. Most importantly, experiments were performed demonstrating that inhibition of T lymphocyte functions by ultra-low levels of IFN-γ, according to the method of the present invention, can be very effectively employed to treat a broad range of major classes of diseases whose pathogenesis involves T cell-mediated immunoreactivity.

Materials and Methods:

Animals: C57BL/6 or Balb/c mice were used in experiments at 6–8 weeks of age. All animal procedures were approved by the Animal Research Committee of the Weizmann Institute of Science (Rehovot, Israel).

Isolation of organs and cells: Spleens and cells were obtained as previously described (Shachar, I. et al., Immunity 1995, 3:373). Enrichment of T cells was performed using the MACS system (Miltenyi Biotec, Auburn Calif.). Spleen cells were incubated with anti-CD45RA (B220) magnetic beads and the $CD45^-$ cells were collected. Helper ($CD4^+$) T cells were enriched using anti-CD4 magnetic beads.

Adhesion assay: Adhesion assays were performed as previously described (Flaishon, L. et al., J. Exp. Med 2000, 192:13 81).

DTH assays: Balb/c mice were sensitized on shaved abdomens with 2% oxazolone in acetone/olive oil. Mice were injected with different doses of immature B cell-conditioned medium or ultra-low levels of IFN-γ, once a day or every other day of the experimental period. Delayed-type hypersensitivity was elicited 6 days later by ear-challenge with 0.5% oxazolone in acetone/olive oil and ear-thickness was measured immediately prior to and 24 h following challenge.

OVA sensitization and challenge: Balb/c mice were immunized intraperitoneally on Days 0, 7, and 14 with 100 μg chicken egg OVA (Sigma, St. Louis, Mo.) mixed with 2 mg of aluminum hydroxide (Pierce, Rockford, Ill.) in 300 μl of 0.9% NaCl. Starting on Day 15 following initial sensitization, animals were challenged daily for 5 days (Days 15–19) with 20 min inhalations of 5% OVA in 0.9% NaCl, using an ultrasonic nebulizer (DeVilbiss, Somerset, Pa.) connected to a 0.5 liter plastic chamber in which the animals were placed for inhalations.

The IFN-γ-treated group was injected intraperitoneally with ultra-low levels of murine IFN-γ (6 units in 500 μl 0.9% NaCl; Genentech, Inc. South San Francisco, Calif.) starting on Day 15 for 5 days, 5 minutes prior to each inhalation.

Measurement of AHR: AHR was measured, as previously described (Djukanovic, R. et al., Am. Rev.Respir. Dis. 1990, 142:434), via enhanced expiratory pause (Penn) in plethysmographic box (Buxco Electronics, Sharon, Conn.) pressure during expiration. Briefly, conscious, spontaneously breathing animals were evaluated in closed plethysmographic chambers and pressure differences were measured between the main chamber of the plethysmograph, containing the animal, and a reference chamber (generating a box pressure signal). Data was expressed using the dimensionless parameter Penn according to the formula: Penn=(Te−Tr) (PEPb)/(Tr*PIPb), where Te is the expiratory time (in seconds), Tr is the relaxation time (time of the decay of the expiratory box pressure to 36% of peak expiratory box pressure in seconds), PEPb is the peak expiratory pressure (in ml/s) and PIPb is the peak inspiratory pressure (in ml/s). Every animal was evaluated following the fifth OVA inhalation (early reaction) and 24 hours later (late reaction).

Bronchoalveolar lavage (BAL): BAL was performed 20 days following the last AHR evaluation using animals deeply anesthetized with Thiopental sod, a 22 gauge needle was inserted into the proximal trachea and secured with a 3–0 silk suture through a midline celiotomy and animals were euthanized by exsanguination through withdrawal of blood from the inferior vena cava. The lungs were lavaged 5 times via the tracheal needle with 1 ml of 0.9% NaCl, BAL fluid samples were collected from each animal and pooled and cell counts were determined using a hemocytometer. Samples were centrifuged, and pellets were resuspended in 0.9% NaCl for application to Cytospin slides.

Lung histology: Lungs were prepared for histology by perfusing animals with 20 ml of PBS followed by inflation with 1 ml of 4% formalin, until distension. Samples were fixed in 4% formalin for 48 hr, tissues were embedded in paraffin and 2–3 $\mu$m sections were cut and stained with hematoxylin and eosin for histochemical analysis.

Cytoskeleton rearrangement assays: T cells were pre-incubated in the presence or absence of ultra-low levels of IFN-$\gamma$, washed, stimulated for 20 s with low levels of SDF-1 (500 ng/ml), promptly fixed by incubation in three volumes of 3.7% paraformaldehyde for 10 min at room temperature. Fixed cells were washed and the membranes permeabilized by incubation for 2 min on ice in a solution containing HEPES (20 mM), sucrose (300 mM), NaCl (50 mM), MgCl$_2$ (3 mM) and Triton-X-100 (0.1%). Membrane-permeabilized cells were stained with the F-actin specific reagent FITC-phalloidin (2 $\mu$g/ml), washed with PBS, and analyzed by flow cytometry.

Hapten induced colitis: To induce colitis, anesthetized Balb/c mice were given enemas with a solution of trinitrobenzene sulfonic acid (TNBS) dissolved in a mixture of PBS (pH 7.2) and then mixed with an equal volume of ethanol, yielding a solution with a final concentration of 2.5% TNBS in 50% ethanol. Mice were administered a dose of 150 mg TNBS/kg body weight on Day 0 and disease severity was scored as a function of weight loss, fur ruffling, rectal prolapse and death.

Experimental Results:

Immature B cell-conditioned medium or ultra-low levels of IFN-$\gamma$ abrogates activation-induced adhesion of T cells to ECM: In order to migrate to secondary lymphoid organs, such as LNs, or to sites of inflammation, T cells must interact extensively with the ECM (Butcher, E. C., and Picker, L. J. Science 1996, 272:60). The method of the present invention therefore employs immature B cell-conditioned medium and ultra-low levels of IFN-$\gamma$ to interfere with such processes to treat disease states. Thus, in order to demonstrate the effectiveness of such a method, the capacity of immature B cell-conditioned medium or ultra-low levels of IFN-$\gamma$ to negatively regulate adhesion of T cells to the ECM was analyzed, as described below.

Figure 6A:
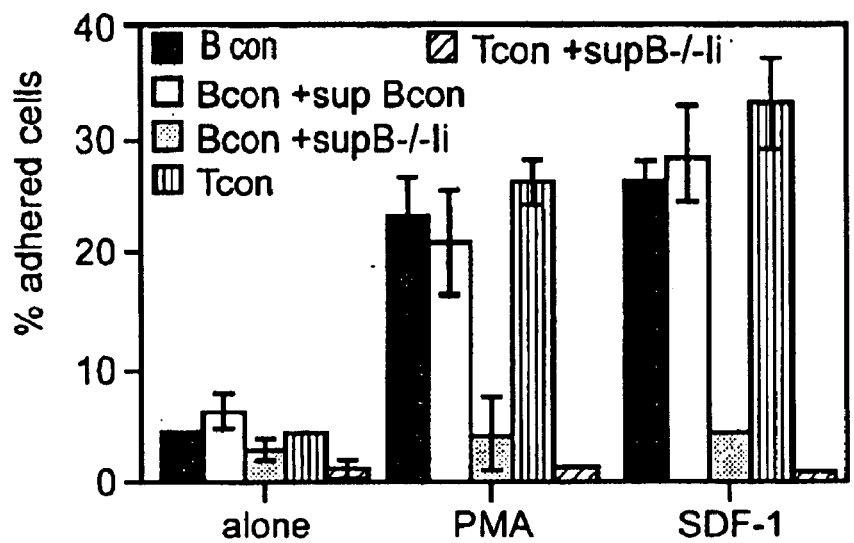
FIG. 6a is a histogram depicting the percentage of PMA- or SDF-1-stimulated T cells adhering to FN-coated plastic tissue culture dishes in the presence of conditioned medium (sup) collected from control (B con) or Ii$^{-/-}$ (B Ii$^{-/-}$) B cells. One representative experiment out of 3 is depicted.
Figure 6B:
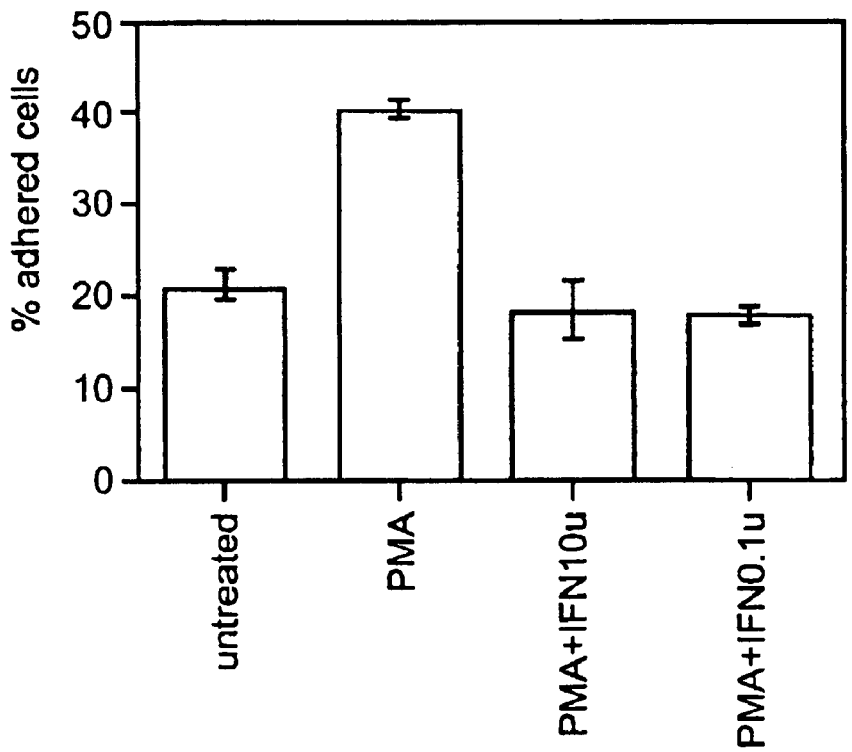
FIG. 6b is a histogram depicting the percentage of PMA-stimulated T cells adhering to FN-coated plastic tissue culture dishes in the presence of 10 or 0.1 unit/ml IFN-γ. One representative experiment out of seven is depicted.

Naïve T cells labelled with $^{51}$Cr were activated with PMA, a potent agonist of integrin mediated adhesion (Shimizu, Y. et al., J. Exp. Med. 1992, 175:577; Faull, R. J. et al., J. Exp. Med. 1994, 179:1307), or SDF-1, a potent T cell chemoattractant (Bleul, C. C. et al., J. Exp. Med. 1996, 184:1101; Bleul, C. C. et al., Nature 1996, 382:829), in the presence of immature B cell-conditioned medium or ultra-low levels of IFN-$\gamma$ (0.1 unit/ml). Upon activation, untreated T cells were observed to dramatically increase their adhesion to FN, whereas such adhesion by cells treated with immature B cell-conditioned medium or ultra-low levels of IFN-$\gamma$ (0.1 unit/ml) was completely abrogated (FIGS. 6a and 6b, respectively).

These results therefore clearly demonstrated the capacity of immature B cell-conditioned medium or ultra-low levels of IFN-$\gamma$ (0.1 unit/ml) to powerfully inhibit adhesion of activated T cells to ECM.

Treatment with immature B cell-conditioned medium or ultra-low levels of IFN-$\gamma$ inhibit migration of T cells to sites of DTH-induced inflammation: The capacity of immature B cell-conditioned medium or ultra-low levels of IFN-$\gamma$ to inhibit T cell migration to in vivo sites of inflammation, according to the method of the present invention, was analyzed by analyzing their effect on the migration to sites of inflammation induced by DTH, an antigen-induced cutaneous inflammatory response involving CD4$^+$ T cell-mediated pathogenesis. Delayed-type hypersensitivity experiments were performed as follows.

Figure 7A:
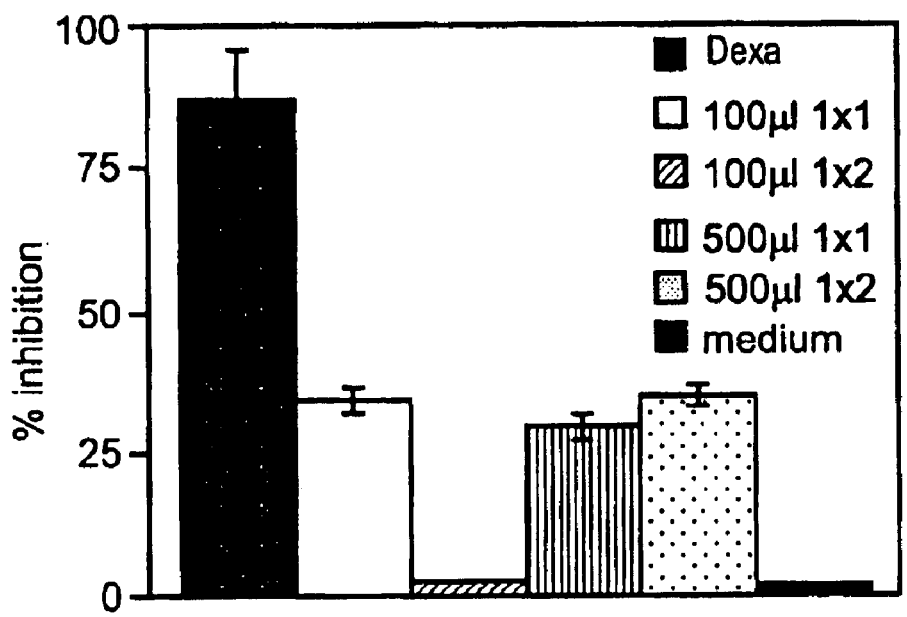
FIGS. 7a–b are histograms depicting the percent inhibition of delayed type hypersensitivity (DTH) response 24 h following ear-challenge of Balb/c mice with 0.5% oxazolone in acetone/olive oil induced by injection of Ii$^{-/-}$ B cell-conditioned medium or by ultra-low levels of IFN-γ. Prior to challenge, mice were injected every day (1×1) or every two days (1×2), for 6 days, with 100 or 500 μl of either Ii$^{-/-}$ B cell-conditioned medium (FIG. 7a) or with IFN-γ at various concentrations (10, 1 and 0.1 units/ml, as indicated.
Figure 7B:
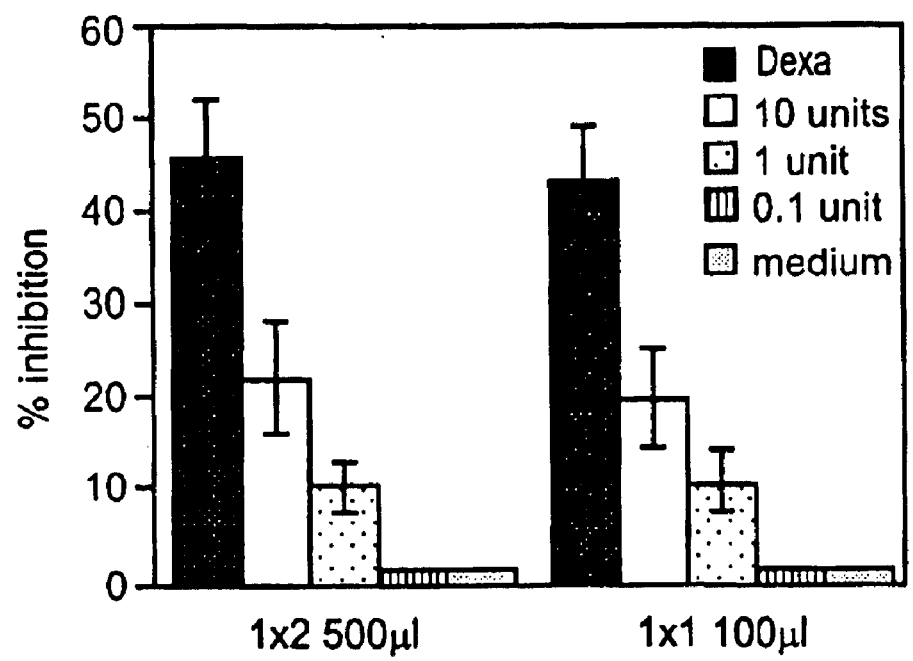

Normal mice were injected with various doses of medium conditioned by incubating Ii$^{-/-}$ B cells or ultra-low levels of IFN-$\gamma$ in FN-coated plates. Treatment of mice with Ii$^{-/-}$ B cell-conditioned medium (FIG. 7a) or ultra-low levels of IFN-$\gamma$ [FIG. 7b; $\geq$4 U/kg body weight (100 $\mu$l×1 unit/ml÷25 g mouse=4 U/kg)] were found to significantly inhibit ear swelling, whereas control medium collected from FN-coated plates had no effect.

These results therefore demonstrated that immature B cell-conditioned medium or ultra-low levels of IFN-$\gamma$ can be employed according to the method of the present invention to significantly inhibit migration of T cells to sites of inflammation in vivo and thereby ameliorate DTH responses.

Treatment with ultra-low levels of IFN-$\gamma$ significantly ameliorates allograft rejection: Transplantation of allogeneic cells, tissues and organs is a method of treatment employed to treat a very broad range of disorders including many life-threatening disorders. Graft rejection, however remains a major cause of transplantation failure, regardless of the use of prophylactic treatments which, even when successfully employed, rely on powerful immunosuppressant drugs producing undesirable side-effects.

Thus, experiments to demonstrate the capacity of ultra-low levels of IFN-$\gamma$, employed according to the method of the present invention, to ameliorate allograft rejection were performed by analyzing mononuclear infiltration into allograft tissue in treated allograft recipient animals, as follows.

Kidney tissue from Balb/c mice (H-2d) was transplanted under the kidney capsule of allogeneic C3H hosts (H-2k) and analyzed by histology for mononuclear infiltration and tissue damage on Days 4 and 7 post-transplant. The C3H hosts were treated with 3 injections of low-dose IFN-$\gamma$ (5 units/d=200 units/kg body weight/day) during the week prior to receiving the allograft, and every other day following transplantation until time of sacrifice. Control animals received injections of RPMI. Mononuclear infiltration was scored by counting cells in a minimum of four high-power ($\times$100) fields in renal graft sections.

Figure 8A:
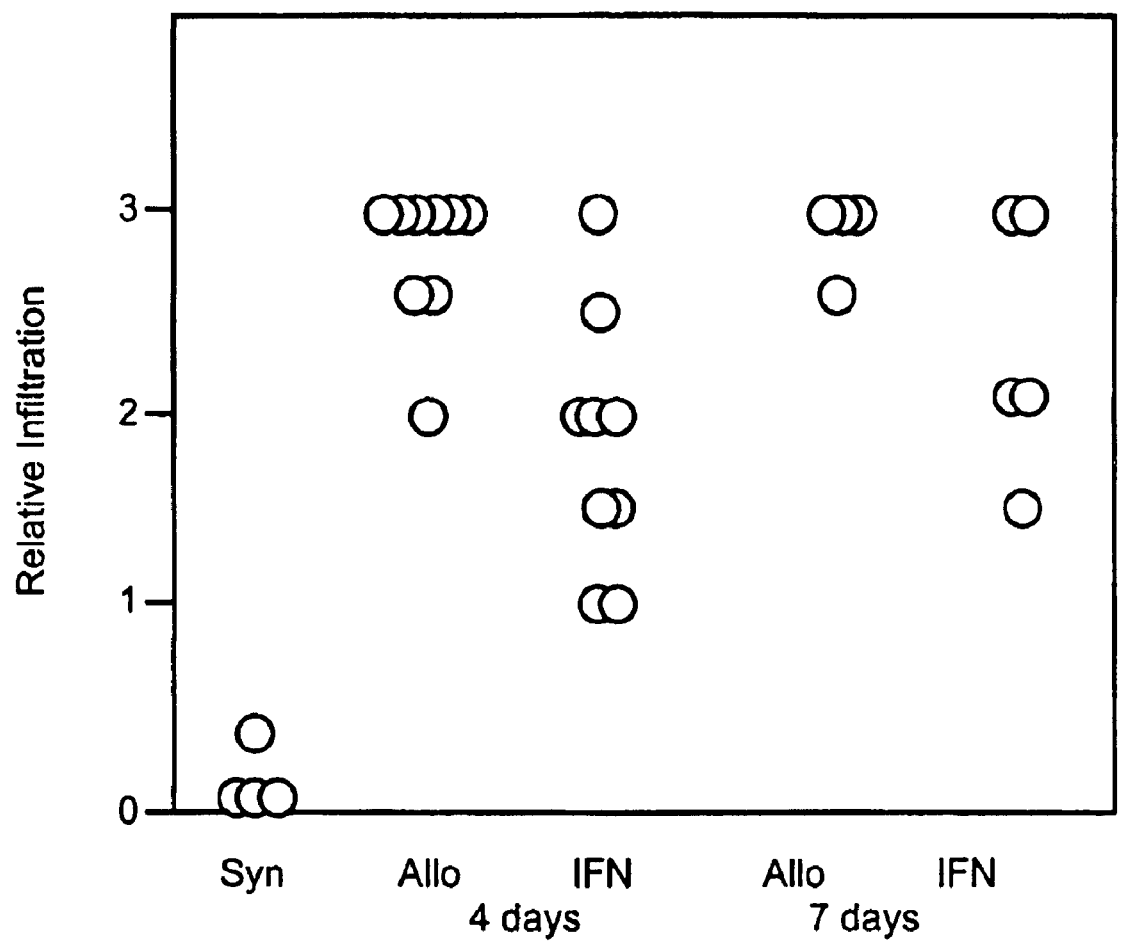

Animals treated with ultra-low levels of IFN-$\gamma$ were found to display greatly reduced levels of mononuclear cell infiltration into allografts on Days 4 and 7 post-transplant, as quantified in FIG. 8a. Histological analysis of allograft tissue on Day 6 post-transplant in animals treated with ultra-low levels of IFN-$\gamma$ very clearly depict a dramatic inhibition of infiltration compared to untreated recipients (FIGS. 8c and 8b, respectively).

These results therefore clearly demonstrated that ultra-low levels of IFN-$\gamma$ can be effectively employed according to the method of the present invention to significantly ameliorate allograft rejection.

Treatment with ultra-low levels of IFN-γ alleviates asthma: Asthma, a widespread disease with often fatal consequences and whose incidence is dramatically on the increase in urban populations around the world, is a chronic inflammatory disorder of the airways that is characterized by intermittent episodes of airway obstruction and wheezing, by variable airflow obstruction, airway hyperresponsiveness (AHR) and airway inflammation. Inflammation in asthmatic lung is characterized by infiltration of the airway wall with mast cells, lymphocytes and eosinophils. Although asthma is multifactorial in origin, recent advances suggest that asthma is an immune disease with a prominent role for T lymphocytes in its pathogenesis. In particular CD4+ T cells producing a Th2 pattern of cytokines have been shown to play a pivotal role in the pathogenesis of this disease (Huang, S. K. et al., J. Immunol. 1995, 155:2688; Robinson, D. S. et al., N. Engl. J. Med. 1992, 326:298; Walker, C. et al., Am. Rev. Respir. Dis. 1992, 146:109; Cohn, L. et al., J. Exp. Med. 1999, 190:1309).

Thus, in order to demonstrate the capacity of ultra-low levels of IFN-γ, employed according to the method of the present invention, to ameliorate Th2-mediated diseases, such as asthma, experiments were performed aimed at inhibiting the migration of Th2 cells in a murine OVA-induced asthma model.

Inhalation of aerosolized OVA was observed to cause peribronchial and perivascular accumulation of inflammatory cells, such as eosinophils and T cells, into the tracheal submucosa of OVA-sensitized Balb/c mice, compared to non-sensitized mice (FIGS. 9b and 9a, respectively). However, treatment with ultra-low levels of IFN-γ (6 units/day=240 units/kg body weight/day) were shown to strikingly prevent such recruitment of antigen-induced inflammatory cells (FIG. 9c). In accordance with these observations, treatment with ultra-low levels of IFN-γ were observed to dramatically inhibit the symptoms of asthma, such as airflow obstruction, AHR and airway inflammation.

These results therefore showed that ultra-low levels of IFN-γ can be successfully employed according to the method of the present invention to treat Th2 cell-promoted diseases, such as asthma.

Treatment with ultra-low levels of IFN-γ significantly ameliorates colitis: Autoimmune diseases of the gastrointestinal tract, such as colitis, are debilitating diseases of widespread incidence whose treatment using prior art techniques remains inefficient, relying on the use of anti-inflammatory drugs, such as steroids, causing significant levels of undesirable side-effects.

Thus, experiments were performed in order to demonstrate the capacity of ultra-low levels of IFN-γ employed according to the method of the present invention to treat Th1 cell-mediated diseases, such as colitis, using a murine TNBS-induced colitis model in which Balb/c mice treated with TNBS develop potentially lethal weight loss and colitis.

Figure 10A:
FIGS. 10a–c are photographs depicting inhibition of TNBS-induced colitis in mice treated with low-levels of IFN-γ. Show are representative colons from untreated mice (FIG. 10a, control), mice treated with TNBS (FIG. 10b, TNBS) and mice treated with TNBS+5 units IFN-γ per day for 3 days (FIG. 10c, TNBS+IFN).
Figure 10B:
Figure 10C:
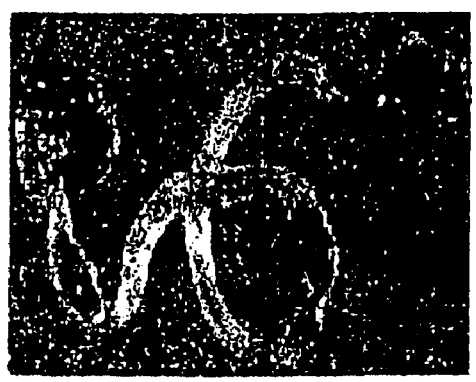

As depicted by visual examination of colons, treatment of TNBS-treated mice with ultra-low levels of IFN-γ (5 units/d=200 units/kg body weight/day) injected i.p. dramatically inhibited the development of colitis, as compared to TNBS-treated mice (FIGS. 10c and 10b, respectively).

These results therefore demonstrated that treatment with ultra-low levels of IFN-γ, according to the method of the present invention, can be employed to effectively treat $T_h1$ lymphocyte-induced inflammatory diseases, such as colitis.

Conclusion:

Overall the data presented in these studies demonstrated that ultra-low doses of IFN-γ, ranging from 4–240 units/kg body weight, have the capacity to downregulate ECM adhesion and migration of T cells and, most importantly, these studies showed that the use of ultra-low levels of IFN-γ, according to the method of the present invention, can be very effectively employed to treat a broad range of inflammatory disorders pathogenesis, such as allograft rejection, allergic diseases, such as asthma, caused by $T_h2$ lymphocytes, DTH and $T_h1$ lymphocyte-mediated autoimmune diseases, such as colitis.

Thus, the method of the present invention represents a very marked improvement over prior art uses of IFN-γ to treat diseases associated with, and/or accompanied by, inflammation since prior art approaches used levels of IFN-γ two to four orders of magnitude higher than those successfully employed in the present invention.

Example 3

Ultra-Low Levels of IFN-γ Downregulate Integrin-Dependent Adhesion of B Cells by Activating a Pathway that Interferes with Cytoskeleton Rearrangement In the above Examples it was shown that immature B cells can actively exclude themselves from antigen-enriched sites by downregulating their integrin-mediated adhesion by autocrine production of IFN-γ. Treatment with immature B cell-conditioned medium or ultra-low levels of IFN-γ, according to the method of the present invention, was shown to be capable of inhibiting ECM adhesion and tissue migration of both B and T lymphocytes and thereby to effectively treat a broad range of major classes of inflammatory diseases, as described in Example 2.

Thus, experiments were performed in order to clearly demonstrate the biochemical and physiological mechanisms by which ultra-low levels of IFN-γ, employed according to the method of the present invention, inhibit the adhesion and migration of lymphocytes and thereby can be effectively employed to treat inflammatory diseases.

Materials and Methods:

Cells: The murine pre-B cell-like lymphoma line, 70Z/3 (Paige, C. J. et al., J. Immunol. 1978, 121:641) was grown in suspension culture at 37° C. in RPMI-1640 medium containing 10% (v/v) FCS and 200 µM β-mercaptoethanol. Primary B cells were obtained from C57BL/6 spleens and were purified by treating splenocyte suspensions with anti-Thy1.2, -CD4, and -CD8 antibody (Southern Biotechnology Associates, USA) followed by low Tox-M complement (Cedarlane, Canada).

Immature B cell-conditioned medium: Conditioned medium was collected from immature B cells from invariant chain-deficient mice (Shachar, I., and Flavell, R. A. Science 1996, 274:106) as previously described (Flaishon, L. et al., J. Exp. Med. 2000, 192:1381).

Adhesion assays: Adhesion assays were performed as previously described (Flaishon, L. et al., J. Exp. Med. 2000, 192:1381).

Transwell migration assays: Chemotaxis was assayed by using transwell chambers (6.5 mm diameter; 5 µm pores) (Corning Inc., Corning N.Y.). Approximately 5×10⁶ 70Z/3 cells were suspended in 1 ml of RPMI supplemented with 0.25% FCS and 100 µl aliquots were placed in the upper compartment of the transwell apparatus and the bottom chamber was filled with 600 µl medium supplemented with 1 µg/ml SDF-1 (PeproTech, Inc., Rocky Hill N.J.). Migration towards SDF-1 in the lower chamber was analyzed after 3 hours by immunofluorescent flow cytometry in the presence or absence of invariant chain-deficient B cell-conditioned medium or of ultra-low levels of IFN-γ. Cells were pre-incubated with anti-INF-γ receptor or anti-CD8 antibodies (Pharmingen) for 2.5 hours prior to transwell assays in blocking experiments.

Preparation of cellular lysates: 70Z/3 cells were pre-incubated with or without immature B cell-conditioned medium or ultra-low levels of IFN-γ in the presence of inhibitors, for 30 minutes, stimulated for 5 minutes with PMA (0.2 μg/ml) and immediately frozen. Frozen cells were thawed and lysed in lysis buffer containing 25 mM Tris (pH 7.4), 2 mM vanadate, 75 mM β-glycophosphate (pH 7.2), 2 mM EDTA, 2 mM EGTA, 10 mM NaPPi, 0.5% NP-40 and the following protease inhibitors: 10 μg/ml Leupeptin, 10 μg/ml aprotinin, 10 μg/ml pepstatin, 10 μg/ml chymostatin (Roche, Switzerland), 1 mM PMSF (Sigma, Israel), and 20 mM N-ethyl-maleimide (Sigma, Israel).

Western immunoblotting analysis: Crude lysates or immunoprecipitates of p-tyr proteins were separated by 10% (w/v) SDS-PAGE and separated proteins were electroblotted onto nitrocellulose membranes. Blotted proteins were probed with anti-p-AKT (Cell Signaling Technology), anti-p-tyr (pTyr99) or anti-PKCα (C-20) antibodies (Santa Cruz) and probed blots were developed by horseradish peroxidase-conjugated anti-mouse or anti-rabbit IgG antibodies (Jackson Labs).

Membrane purification: Cell suspension aliquots of $10^7$ cells were incubated in PBS containing 5 μg/ml digitonin (Sigma, Israel) for 5 min on ice, centrifuged and pellets were resuspended in lysis buffer, as described above.

Analysis of cytoskeletal rearrangement: Primary B cells or 70Z/3 cells were pre-incubated for 30 min in with or without immature B cell-conditioned medium or ultra-low levels of IFN-γ (0.1 unit/ml) in the presence of absence of the PI-3-K inhibitors wortmannin or LY. Pre-incubated cells were washed, stimulated SDF-1 (500 ng/ml) for 20 sec and immediately fixed by incubation in three volumes of 3.7% paraformaldehyde for 10 min at room temperature. Fixed cells were washed and the membranes were permeabilized for 2 min on ice in a solution containing 20 mM HEPES, 300 mM sucrose, 50 mM NaCl, 3 mM $MgCl_2$, and 0.1% Triton X-100. Finally, membrane-permeabilized cells were stained with the F-actin specific reagent FITC-phalloidin (2 μg/ml), washed with PBS and analyzed by flow cytometry. The percent increase of polymerized actin=[(mean of polymerized actin in activated cells)–(mean of polymerized actin in non-activated cells)]÷(mean of polymerized actin in activated cells)×100%.

Inhibitors: The PI-3-K inhibitors (CalBiochem) and corresponding concentrations employed were wortmannin (100 nM) and LY (200 mM). The PKC inhibitors used were: PKCα/β pseudosubstrate (10 μM; BioMol research laboratories) myristoylated-AIP, CaM kinase II inhibitor (10 μg/ml; BioMol research laboratories); the PKCδ inhibitor rottlerin (5 μM; CalBiochem); and the PKC inhibitor GF109203X (0.5 μM; CalBiochem). The p38 inhibitor SB203580 (SB) and the MEK inhibitor PD98059 (PD) were used at concentrations of 10 μM and 25 μM, respectively.

Experimental Results:

A cell line model for inhibition of B cell migration by ultra-low levels of IFN-γ: In order to conveniently analyze the mechanisms by which ultra-low levels of IFN-γ inhibit adhesion and migration of lymphocytes according to the method of the present invention, experiments were performed to identify a B cell line that could increase its adhesion and migration in response to chemokine stimulation and in which such responses could be inhibited by ultra-low levels of IFN-γ, thereby constituting a realistic model of such lymphocyte functions.

Figure 11A:
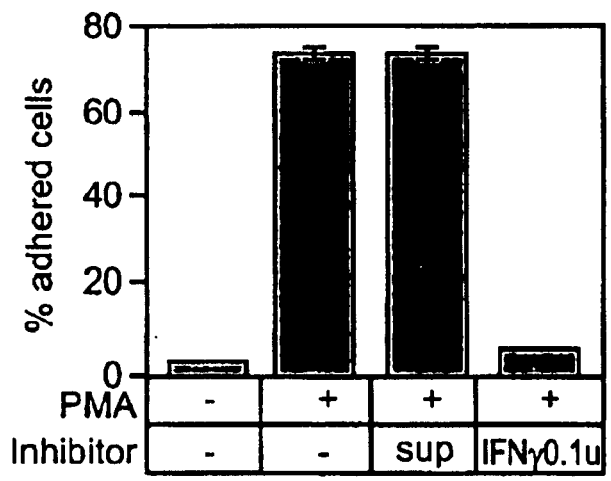
FIG. 11a is a histogram depicting percentage of PMA (0.2 μg/ml) stimulated 70Z/3 cells adhering to FN-coated plastic tissue culture dishes following 30 min of incubation in the presence of immature B cell-conditioned medium (sup) or ultra-low levels of IFN-γ (0.1 unit/ml).
Figure 11B:
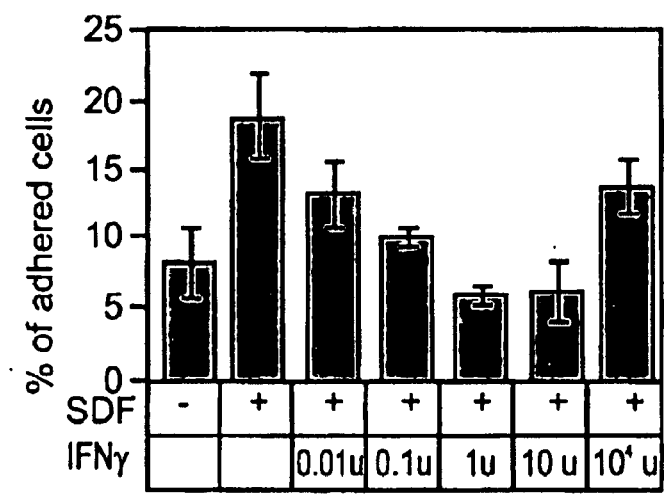
FIG. 11b is a histogram depicting the percentage of SDF-1 (50 μg/ml) stimulated 70Z/3 cells adhering to FN-coated plastic tissue culture dishes following 30 min of incubation in the presence of different concentrations of IFN-γ, as indicated (units/ml). One representative experiment out of five is depicted

The 70Z/3 murine pre-B lymphoma cell line was identified as meeting these requirements. Following PMA or SDF-1 (FIG. 10b) stimulation, these cells were found to increase their adhesion to FN, whereas immature B cell-conditioned medium and ultra-low levels of IFN-γ (0.1 unit/ml) were found to significantly inhibit this adhesion response (FIG. 11a). Similarly, ultra-low levels of IFN-γ (1 unit/ml) were found to efficiently and optimally downregulate SDF-1 stimulated adhesion responses (FIG. 11b).

Figure 11C:
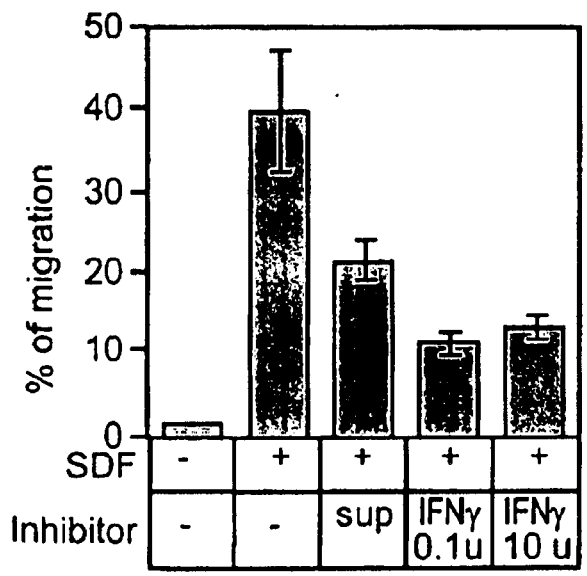
FIG. 11c is a histogram depicting the percentage of 70Z/3 cells migrating towards SDF-1 in 24-well transwell plates following 30 min of incubation in the presence of immature B cell-conditioned medium (sup) or different concentrations of IFN-γ, as indicated (units/ml). The data depict one representative experiment out of three.

The ability of immature B cell-conditioned medium and ultra-low levels of IFN-γ to inhibit the transwell migration of 70Z/3 cells toward the chemokine SDF-1 was also confirmed. As shown in FIG. 11c, cells pre-incubated with immature B cell-conditioned medium and, in particular, with ultra-low levels of IFN-γ (0.1 unit/ml) markedly downregulated their migration toward SDF-1.

Thus, similarly to primary B cells, 70Z/3 cells respond to activation-induced pro-adhesive stimuli and such responses in these cells are sensitive to inhibition by immature B cell-conditioned medium and ultra-low levels of IFN-γ. Such cells therefore constitute an appropriate model system to investigate the inhibitory signaling pathways induced by ultra-low levels of IFN-γ.

Ultra-low levels of IFN-γ inhibit lymphocyte adhesion and migration via an IFNR-activated signaling cascade: To determine whether the IFN-γ-induced inhibition of cell adhesion and migration is initiated by the IFN-γ receptor (IFNR) (Stark, G. R. et al., Annu. Rev. Biochem. 1998, 67:227; Bach; E. et al., Annu. Rev. Immunol. 1997, 15:563) or by a novel receptor not previously described, the involvement of this receptor in the inhibitory pathway was investigated as follows.

Analysis of adhesion to FN was performed by pre-treating 70Z/3 cells for 3 h with anti-IFNR or anti-CD8 antibodies, washing the cells followed by stimulation with PMA in the presence or absence of immature B cell-conditioned medium or ultra-low levels of IFN-γ (0.1 unit /ml).

Figure 12A:
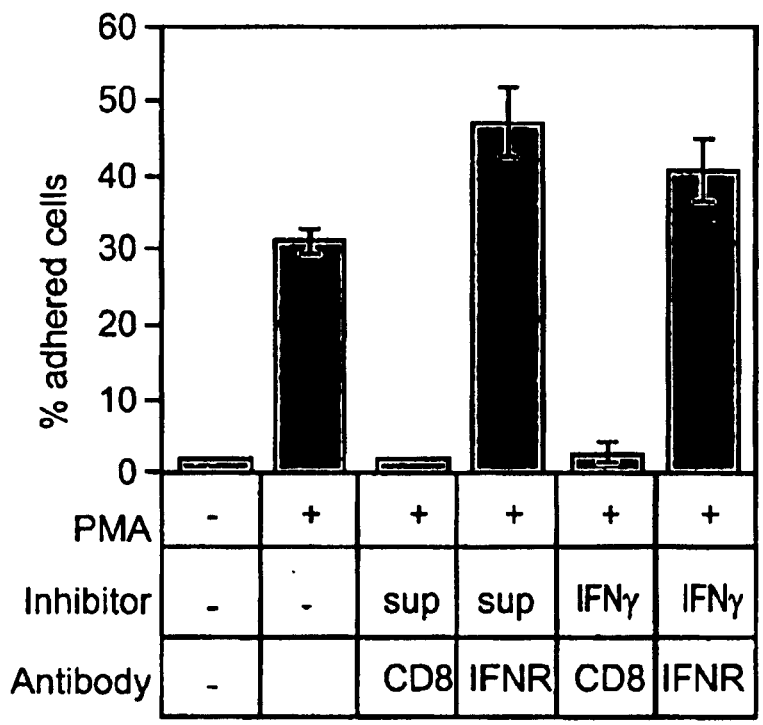
FIG. 12a is a histogram depicting the percentage of PMA (0.2 μg/ml) stimulated 70Z/3 cells adhering to FN-coated plastic tissue culture dishes following 30 min of incubation in the presence of immature B cell-conditioned medium (sup) or ultra-low levels of IFN-γ (0.1 unit/ml) following pre-treatment for 2.5 h with anti-CD8 or -IFNR antibody. One representative experiment out of three is depicted.

As shown in FIG. 12a, whereas anti-CD8 control antibody did not influence inhibition of adhesion to FN mediated by immature B cell-conditioned medium or by ultra-low levels of IFN-γ, neutralizing anti-IFNR antibody was observed to strikingly abrogate these inhibitory effects.

To further demonstrate that ultra-low levels of IFN-γ similarly inhibit cellular migration via IFNR, the transwell migration of 70Z/3 cells towards SDF-1 was monitored in the presence of neutralizing anti-IFNR antibody.

Figure 12B:
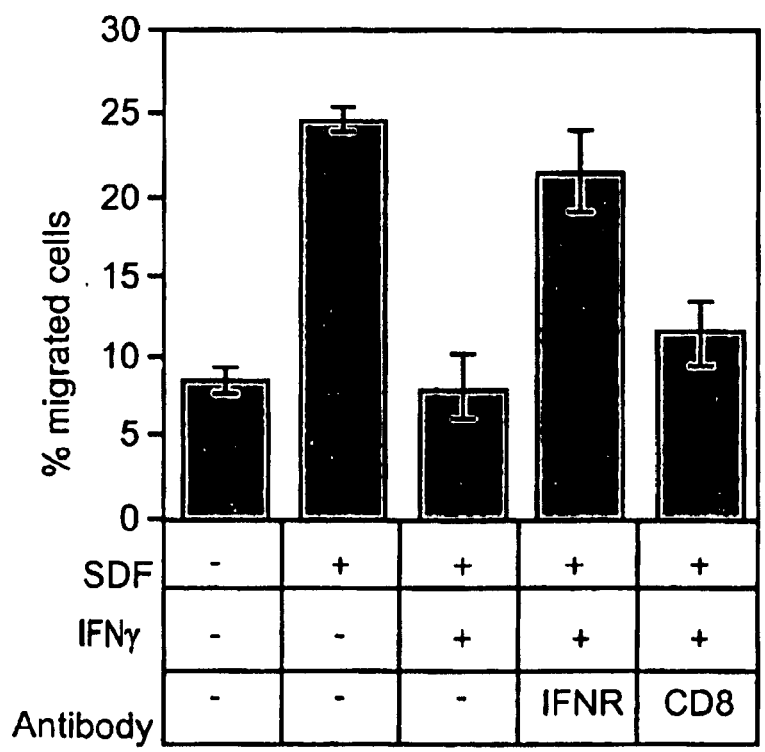
FIG. 12b is a histogram depicting the percentage of 70Z/3 cells migrating towards SDF-1 in 24-well transwell plates following 30 min of incubation in the presence or absence of ultra-low levels of IFN-γ (0.1 unit/ml) following pre-treatment for 3 h with anti-CD8 or -IFNR antibody. Migration was analyzed by immunofluorescent flow cytometry and the data depict one representative experiment out of three.

Indeed, inhibition of cell migration towards SDF-1 mediated by ultra-low levels of IFN-γ (0.1 unit/ml) was found to be abrogated in cells pre-treated with neutralizing anti-IFNR antibody but not in cells pre-treated with control anti-CD8 antibody (FIG. 12b).

These experiments therefore demonstrated that ultra-low levels of IFN-γ or immature B cell-conditioned medium, employed according to the method of the present invention, inhibit adhesion of lymphocytes via signaling cascades initiated by IFNR and, furthermore, that ultra-low levels of IFN-γ also inhibit migration of lymphocytes via signaling cascades initiated by the IFNR.

Ultra-low levels of IFN-γ activate PI-3-K dependent pathways downstream of IFNR: To monitor downstream molecules involved in inhibition of lymphocyte adhesion induced by immature B cell-conditioned medium and ultra-low levels of IFN-γ, the effects of various signal transduction inhibitors on adhesion of activated lymphocytes were analyzed.

Figure 13A:
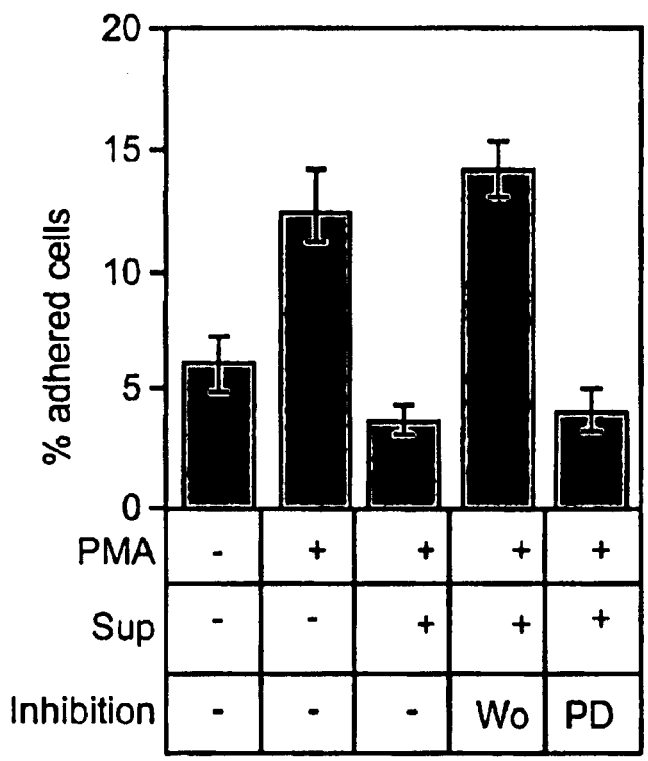
FIG. 13a is a histogram depicting the percentage of PMA (0.2 μg/ml) stimulated 70Z/3 cells adhering to FN following 30 min of incubation in the presence of immature B cell-conditioned medium (sup) and wortmannin (Wo) and PD. One representative experiment out of three is depicted.
Figure 13B:
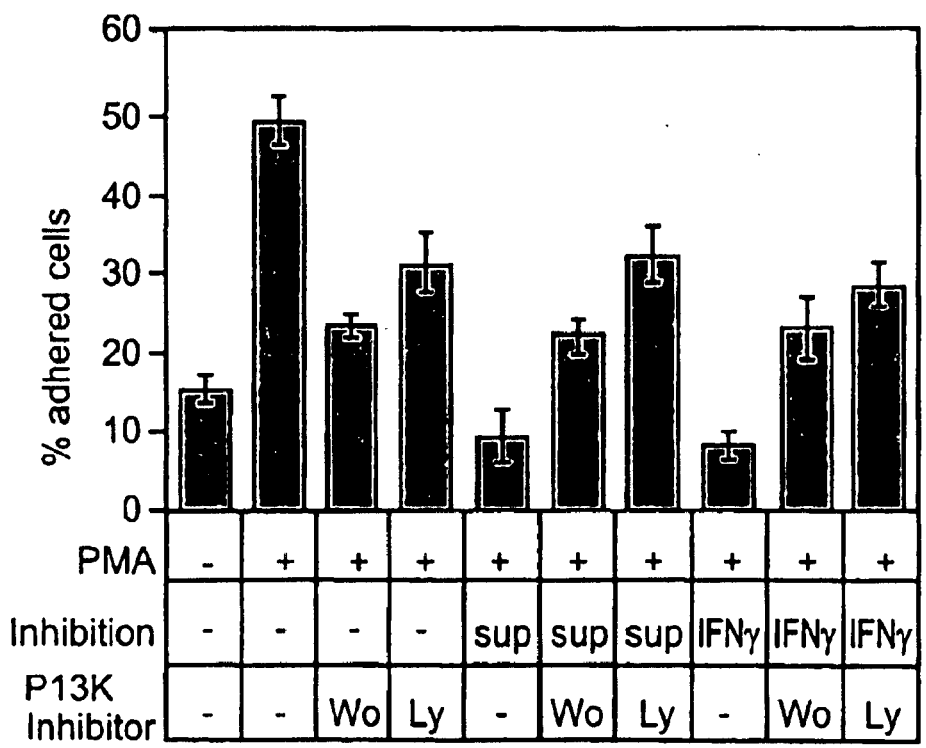
FIG. 13b is a histogram depicting the percentage of PMA (0.2 μg/ml) stimulated 70Z/3 cells adhering to FN-coated plastic tissue culture dishes following 30 min of incubation in the presence of immature B cell-conditioned medium (sup) or ultra-low levels of IFN-γ (0.1 unit/ml) and the PI-3-K inhibitors wortmannin (Wo) and LY294002 (Ly). One representative experiment out of three is depicted.

Whereas the p38 inhibitor SB (data not shown) and the MEK inhibitor PD were not observed to affect inhibition of adhesion of PMA stimulated B lymphocytes to FN by immature B cell-conditioned medium, in the presence of the PI-3-K inhibitor wortmannin, such inhibition of adhesion was fully reversed (FIG. 13a). The ability of the PI-3-K inhibitors wortmannin and LY to reverse inhibition of lymphocyte adhesion to FN by ultra-low levels of IFN-γ was analyzed. As previously described, PI-3-K inhibitors on their own were found to slightly suppress SDF-1 stimulated adhesion of 70Z/3 cells (Wang, J. F. et al., Blood 2000, 95:2505). However, wortmannin and LY were observed to reverse the inhibitory effects of immature B cell-conditioned medium and ultra-low levels of IFN-γ (0.1 unit/ml) on adhesion of PMA-activated B lymphocytes to FN. Cells activated with PMA and treated with either immature B cell-conditioned medium or ultra-low levels of IFN-γ (0.1 unit/ml) in the presence of these PI-3-K inhibitors were observed to adhere to FN similarly to cells activated with PMA in the presence of wortmannin or LY (FIG. 13b). These results therefore demonstrate a potential role for PI-3-K mediated signaling in such cellular adhesion.

To confirm the involvement of PI-3-K in inhibition of adhesion by ultra-low levels of IFN-γ, experiments were performed in order to determine whether the kinase Akt, a known downstream intermediate of the PI-3-K pathway (Burgering, B. M., and Coffer, P. J. Nature 1995, 376:599), is activated by such ultra-low levels of IFN-γ.

As shown in FIG. 13c, in the presence of ultra-low levels of IFN-γ (0.1 unit/ml) increased Akt phosphorylation was observed, thus providing support for a role for PI-3-K in mediating inhibition of lymphocyte adhesion via triggering of IFNR by ultra-low levels of IFN-γ employed according to the method of the present invention.

In order to identify downstream intermediates involved in signaling triggered by ultra-low levels of IFN-γ, experiments were performed to identify proteins whose tyrosine phosphorylation levels could be altered in response to PMA stimulation of 70Z/3 cells and in which such alterations could be inhibited by ultra-low levels of IFN-γ. To identify such candidate proteins, 70Z/3 cells were pre-incubated in the presence or absence of immature B cell-conditioned supernatant or ultra-low levels of IFN-γ for 30 min, subjected to 5 min of PMA stimulation and promptly frozen. Cells were thawed, protein lysates were prepared and these were analyzed for the presence of tyrosine phosphorylated proteins by Western immunoblot analysis.

An 85 kD protein was found to be significantly phosphorylated following PMA induction, and such phosphorylation was found to be completely abrogated when the cells were stimulated in the presence of ultra-low levels of IFN-γ (0.1 unit/ml) and significantly reduced when the cells were stimulated in the presence of immature B cell-conditioned medium (FIGS. 14a and 14b, respectively). These results suggested that phosphorylation of this protein was involved in mediating adhesion of stimulated lymphocytes to ECM and that signaling pathways triggered by ultra-low levels of IFN-γ employed according to the method of the present invention could interfere with such phosphorylation and thereby with cellular adhesion.

To identify this protein, the phosphorylation of various known proteins with a molecular weight of approximately 85 kD was examined. Proteins from PMA-stimulated or non-stimulated cells, which were incubated in the presence or absence of ultra-low levels of IFN-γ (0.1 unit/ml), were immunoprecipitated with anti-phosphotyrosine antibody and analyzed by Western immunoblotting with a panel of antibodies specific for known proteins with a molecular weight of approximately 85 kD.

As shown in FIG. 14c, phosphorylation of PKCα observed following PMA stimulation of cells could be completely abrogated when cells were stimulated in the presence of ultra-low levels of IFN-γ (0.1 unit/ml) and almost completely inhibited when stimulated in the presence of immature B cell-conditioned medium. In addition, wortmannin treatment of cells stimulated in the presence of ultra-low levels of IFN-γ (0.1 unit/ml) was found to reverse inhibition of PKCα phosphorylation (FIG. 14d).

These results thus provided further support to the aforementioned observations suggesting involvement of PI-3-K in inhibition of adhesion induced by ultra-low levels of IFN-γ employed according to the method of the present invention.

To further demonstrate that PKCα is involved in the adhesion of stimulated 70Z/3 cells to FN, its presence in purified membranes following stimulation was analyzed.

Figure 14F:
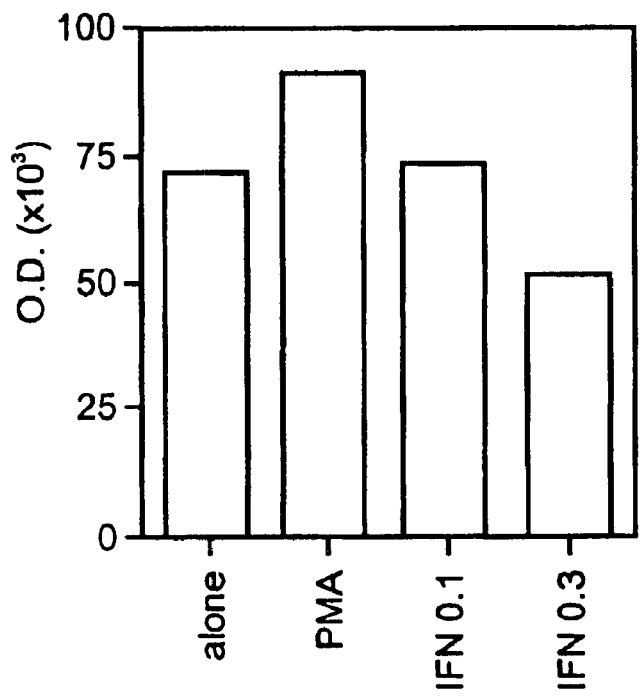

Following PMA stimulation, PKCα levels were indeed found, via Western immunoblotting assay, to be elevated in the membrane fraction and this recruitment was found to be inhibited by ultra-low levels of IFN-γ (0.1 and 0.3 units/ml), as depicted by direct visual and densitometric analysis of the immunoblots (FIGS. 14e and 14f, respectively).

Figure 14G:
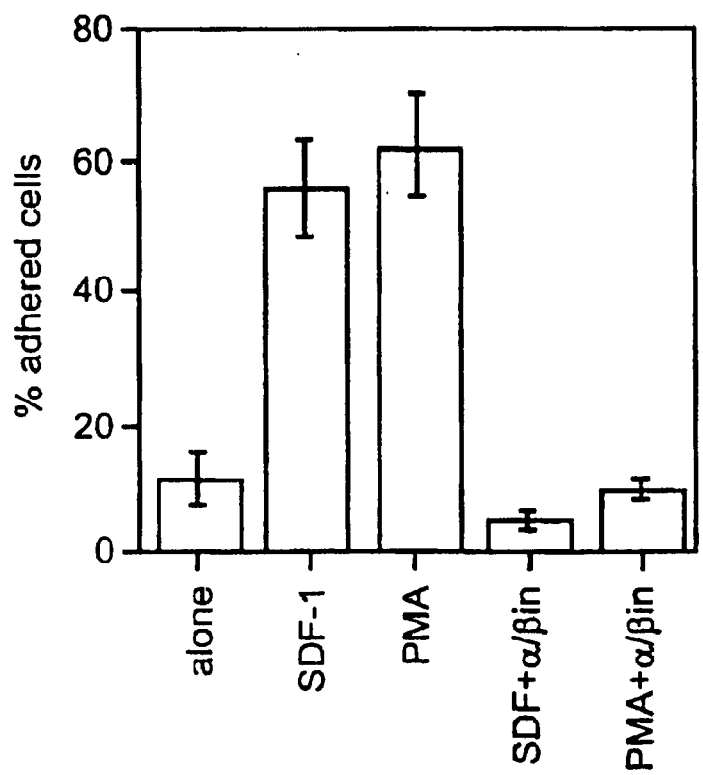
FIG. 14g is a histogram depicting the percentage of SDF-1 or PMA (0.2 μg/ml) stimulated 70Z/3 cells adhering to FN-coated plastic tissue culture dishes following pre-incubation for 1 h in the presence of PKCα/β pseudosubstrate inhibitor. One representative experiment out of three is depicted.

Thus, ultra-low levels of IFN-γ employed according to the method of the present invention inhibit both membrane recruitment and phosphorylation of PKCα which appear to be involved in the adhesion response of PMA stimulated 70Z/3 cells. Consistent with this notion, PKCα/β pseudosubstrate inhibitor was observed to dramatically downregulate adhesion of PMA or SDF-1 stimulated cells to FN (FIG. 14g).

In summary, these experiments demonstrate that inhibition of adhesion of lymphocytes by immature B cell-conditioned medium or ultra-low levels of IFN-γ, employed according to the method of the present invention, is mediated by IFNR via activation of PI-3-K, phosphorylation of the kinase Akt and inhibition of PKCα phosphorylation and membrane recruitment.

Ultra-low levels of IFN-γ inhibit adhesion and migration of lymphocytes via inhibition of cytoskeletal rearrangements: Among the requirements for inducible integrin-mediated adhesion are an increased rate of actin polymerization and extensive reorganization of the actin-based cytoskeleton. Chemokine stimulation is known to promote a rapid burst of actin polymerization, which peaks at 30 sec to 1 min and subsides to baseline levels within 5 to 10 minutes post-stimulation. Thus, experiments were performed in order to determine whether inhibition of adhesion induced by ultra-low levels of IFN-γ employed according to the method of the present invention involves inhibition of such actin polymerization, as follows.

Briefly, 70Z/3 cells were pre-incubated in the presence or absence of ultra-low levels of IFN-γ, pre-incubated cells were stimulated by SDF-1 and immediately fixed with paraformaldehyde, fixed cells were permeabilized and labelled for F-actin with FITC-phalloidin and subjected to flow cytometric analysis.

Figure 15A:
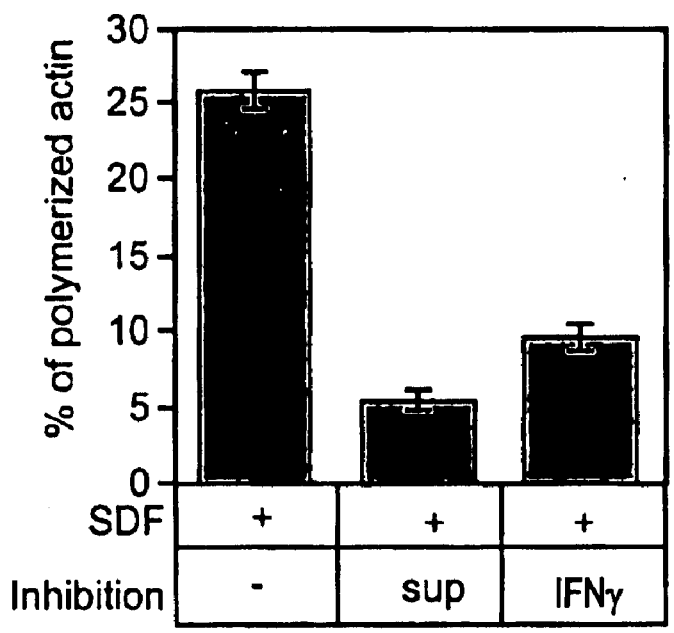
FIG. 15a is a histogram depicting percent actin polymerization in 70Z/3 cells pre-treated with immature B cell-conditioned medium (sup) or ultra-low levels of IFN-γ (0.1 unit/ml) for 30 min and subsequently stimulated with SDF-1. Following this treatment, the cells were fixed and permeabilized, intracellular F-actin was stained with FITC-phalloidin and labelled cells were analyzed by immunofluorescent flow cytometry.
Figure 15B:
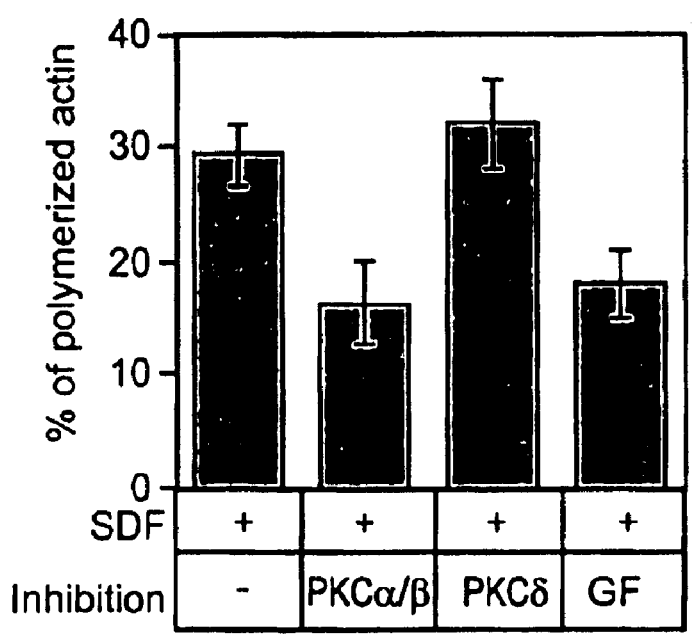
FIG. 15b is a histogram depicting percent actin polymerization in 70Z/3 cells pre-treated with PKC inhibitors for 1 h and subsequently stimulated with SDF-1. Following this treatment, the cells were fixed and permeabilized, intracellular F-actin was stained with FITC-phalloidin and labelled cells were analyzed by immunofluorescent flow cytometry.

As shown in FIG. 15a, SDF-1 stimulation induced actin polymerization, which was greatly downregulated by immature B cell-conditioned medium or ultra-low levels of IFN γ (0.1 unit/ml).

These results therefore demonstrated that ultra-low levels of IFN-γ (0.1 unit/ml), employed according to the method of the present invention, inhibit cell adhesion via inhibition of cytoskeletal rearrangement.

Both the PKC inhibitor GF109203X and PKCα/β pseudosubstrate inhibitor were found to block actin polymerization induced by SDF-1, while PKCδ inhibitor did not have any effect (FIG. 15d), thus demonstrating that PKCα is indeed an essential downstream intermediate involved in SDF-1-induced adhesion and migration of lymphocytes.

Figure 15C:
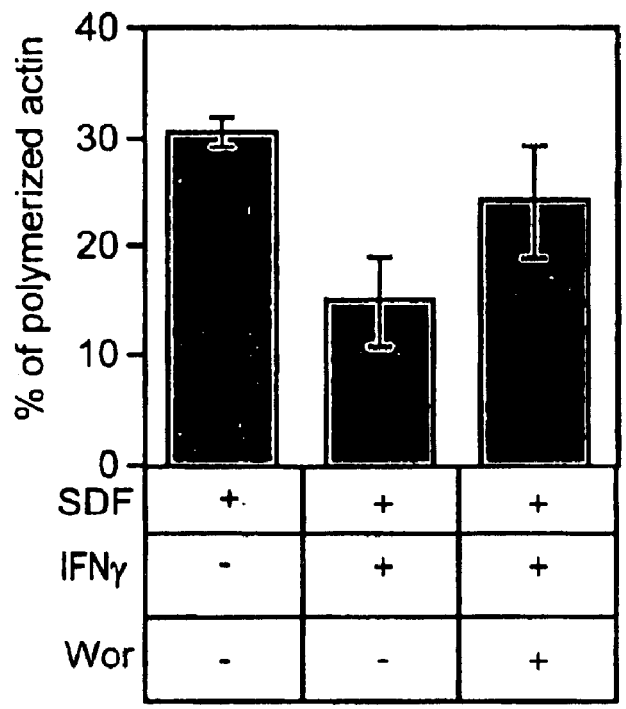
FIG. 15c is a histogram depicting percent actin polymerization in 70Z/3 cells pre-treated with IFN γ (0.1 unit/ml) in the presence of wortmannin (wor) for 30 min and subsequently stimulated with SDF-1. Following this treatment, the cells were fixed and permeabilized, intracellular F-actin was stained with FITC-phalloidin and labelled cells were analyzed by immunofluorescent flow cytometry.
Figure 15D:
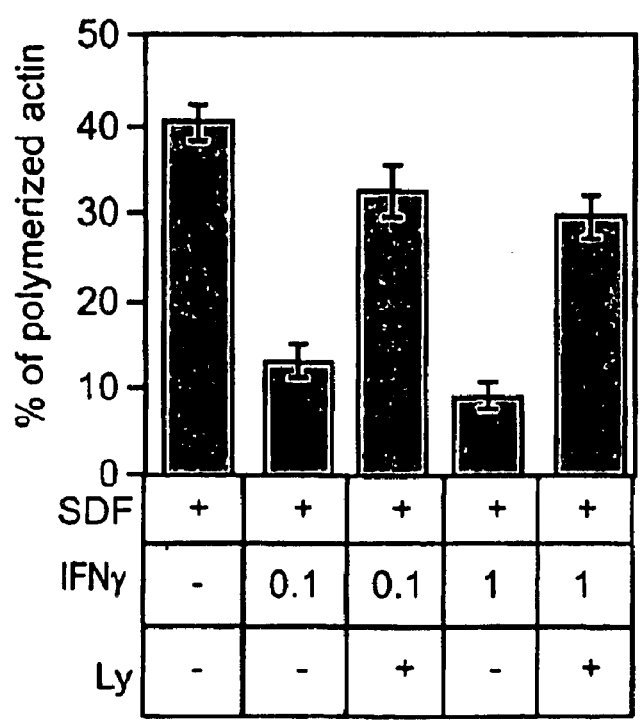
FIG. 15d is a histogram depicting percent actin polymerization in 70Z/3 cells pre-treated with IFN γ (0.1 or 1 unit/ml) in the presence of LY29004 (LY) for 30 min and subsequently stimulated with SDF-1. Following this treatment, the cells were fixed and permeabilized, intracellular F-actin was stained with FITC-phalloidin and labelled cells were analyzed by immunofluorescent flow cytometry.

As shown in FIGS. 15c and 15d, respectively, inhibition of actin polymerization induced by ultra-low levels of IFN-γ (0.1 unit/ml), employed according to the method of the present invention, could be reversed by the PI-3-K inhibitors wortmannin and LY, thereby restoring the adhesion response of the cells as shown above in FIG. 13b.

These results thus demonstrated that immature B cell-conditioned medium or ultra-low levels of IFN-γ, employed according to the method of the present invention, inhibit lymphocyte adhesion via activation of PI-3-K dependent pathways involved in downregulation of actin polymerization.

Finally, in order to demonstrate that ultra-low levels of IFN-γ inhibit adhesion of primary B cells, according to method of the present invention, via the signaling pathways described above in 70Z/3 cells, the roles of PI-3-K and PKCα in the polymerization of actin in primary B cells was analyzed.

Figure 16A:
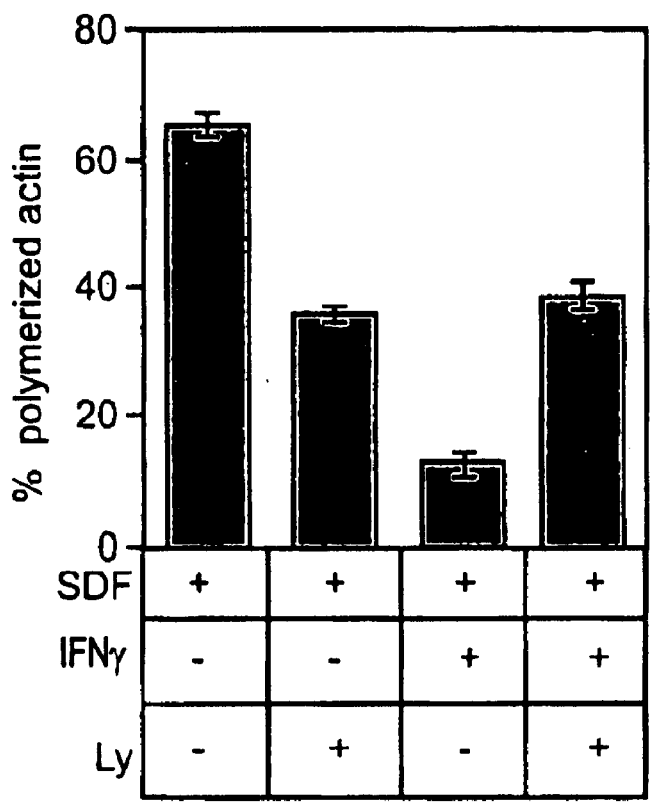
FIG. 16a is a histogram depicting percent actin polymerization in primary B cells pre-treated with ultra-low levels of IFN-γ (0.1 unit/ml) in the presence of LY for 30 min and subsequently stimulated with SDF-1. Following this treatment, the cells were fixed and permeabilized, intracellular F-actin was stained with FITC-phalloidin and labelled cells were analyzed by immunofluorescent flow cytometry.
Figure 16B:
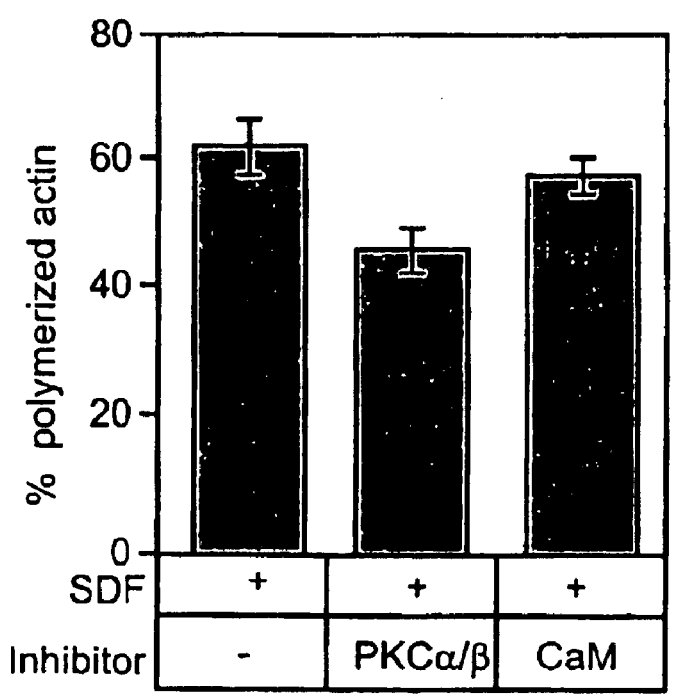
FIG. 16b is a histogram depicting percent actin polymerization in primary B cells pre-treated for 1 h with PKCα/β or CaM kinase II inhibitors (CaM) and subsequently stimulated with SDF-1. Following this treatment, the cells were fixed and permeabilized, intracellular F-actin was stained with FITC-phalloidin and labelled cells were analyzed by immunofluorescent flow cytometry.

Similarly to the responses observed in 70Z/3 cells, ultra-low levels of IFN-γ were shown to strikingly downregulate actin polymerization of SDF-1 stimulated B splenocytes. Such inhibition was shown be reversed in the presence of the PI-3-K inhibitor LY (FIG. 16a). In addition, the PKCα/β pseudosubstrate was shown to be capable of downregulating SDF-1 induced actin polymerization, whereas a control peptide, an inhibitor of CaM kinase II, had no effect on this response (FIG. 16b).

These results therefore demonstrated that ultra-low levels of IFN-γ employed according to the method of the present invention inhibit cytoskeletal rearrangement in primary B cells via activation of PI-3-K, which results in inhibition of PKCα phosphorylation and its dependent signaling pathways and that therefore such inhibition of cytoskeletal rearrangement mediates inhibition of adhesion of primary B cells by ultra-low levels of IFN-γ, as was shown to be the case for 70Z/3 cells.

Conclusion: The results described in this example demonstrate the biochemical and physiological mechanisms whereby, according to the method of the present invention, ultra-low levels of IFN-γ or immature B cell-conditioned medium inhibit lymphocyte adhesion, and hence migration, and can thereby be employed to effectively treat a broad range of diseases whose pathogenesis involves lymphocyte-mediated inflammation. Inhibition of lymphocyte functionality via ultra-low levels of IFN-γ was shown to result from inhibition of cytoskeletal rearrangement mediated via signaling pathways initiated by IFNR involving PI-3-K, phosphorylation of the kinase Akt and inhibition of PKCα phosphorylation and recruitment to the membrane.

The anti-inflammatory consequences of the signaling pathways initiated by ultra-low levels of IFN-γ highlight the advantages of employing IFN-γ therapeutically according to the method of the present invention over prior art uses thereof, which prior art uses involve the use of high doses of IFN-γ which are pro-inflammatory and have been shown to produce a high incidence of undesirable side-effects when applied therapeutically.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

What is claimed is:

1. A method of preventing or reducing an inflammation, the method comprising locally or systemically administering to a subject in need thereof interferon-gamma in an amount so as to achieve an interferon-gamma bulk tissue concentration at a site of inflammation of 0.1–0.14 units per kilogram body weight, thereby preventing or reducing the inflammation in said subject.

2. The method of claim 1, wherein said bulk tissue concentration is 0.1–0.13 units per kilogram body weight.

3. The method of claim 1, wherein said bulk tissue concentration is 0.1–0.12 units per kilogram body weight.

4. The method of claim 1, wherein said bulk tissue concentration is 0.1–0.11 units per kilogram body weight.

5. The method of claim 1 wherein said bulk tissue concentration is 0.1 units per kilogram body weight.

6. The method of claim 1, wherein said concentration is sufficiently low so as to avoid unwanted side-effects associated with interferon-gamma administration.

7. The method of claim 6, wherein said unwanted side-effects are selected from the group consisting of fever, chills, flu symptoms, bone pain, muscle pain, anorexia, fatigue, nausea, vomiting, leukopenia, diarrhea, fatigue, abnormal liver function, black, tarry stools; blood in urine, blood in stools, confusion, cough, hoarseness, loss of balance control, mask-like face, painful urination, difficult urination, pinpoint red spots on skin, shuffling walk, stiffness of arms, stiffness of legs, trembling of hands, shaking of hands, trembling of fingers, shaking of fingers, trouble in speaking, trouble in swallowing, trouble in thinking, trouble in concentrating, trouble in walking, unusual bleeding, unusual bruising, general feeling of discomfort, general feeling of illness, headache, skin rash, unusual tiredness, back pain, side-pain, dizziness, joint pain, loss of appetite and weight loss.

8. The method of claim 1, wherein the inflammation is associated with an inflammatory disease, disorder or condition.

9. The method of claim 8, wherein the inflammatory disease is selected from the group consisting of chronic inflammatory disease and acute inflammatory disease.

10. The method of claim 1, wherein the inflammation is associated with an allergic disease.

11. The method of claim 10, wherein said allergic disease is selected from the group consisting of asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

12. A method of preventing or reducing an inflammation in a subject, the method comprising locally or systemically administering daily to a subject in need thereof interferon-gamma in an amount so as to achieve an interferon-gamma bulk tissue concentration at a site of inflammation of 0.1–0.14 units per kilogram body weight, thereby preventing or reducing the inflammation in said subject.

13. The method of claim 12, wherein said bulk tissue concentration is 0.1–0.13 units per kilogram body weight.

14. The method of claim 12, wherein said bulk tissue concentration is 0.1–0.12 units per kilogram body weight.

15. The method of claim 12, wherein said bulk tissue concentration is 0.1–0.11 units per kilogram body weight.

16. The method of claim 12, wherein said bulk tissue concentration is 0.1 units per kilogram body weight.

17. The method of claim 12, wherein said concentration is sufficiently low so as to avoid unwanted side-effects associated with interferon-gamma administration.

18. The method of claim 17, wherein said unwanted side-effects are selected from the group consisting of fever, chills, flu symptoms, bone pain, muscle pain, anorexia, fatigue, nausea, vomiting, leukopenia, diarrhea, fatigue, abnormal liver function, black, tarry stools; blood in urine, blood in stools, confusion, cough, hoarseness, loss of balance control, mask-like face, painful urination, difficult urination, pinpoint red spots on skin, shuffling walk, stiffness of arms, stiffness of legs, trembling of hands, shaking of hands, trembling of fingers, shaking of fingers, trouble in speaking, trouble in swallowing, trouble in thinking, trouble in concentrating, trouble in walking, unusual bleeding, unusual bruising, general feeling of discomfort, general feeling of illness, headache, skin rash, unusual tiredness, back pain, side-pain, dizziness, joint pain, loss of appetite and weight loss.

19. The method of claim 12, wherein the inflammation is associated with an inflammatory disease, disorder or condition.

20. The method of claim 19, wherein the inflammatory disease is selected from the group consisting of chronic inflammatory disease and acute inflammatory disease.

21. The method of claim 12, wherein the inflammation is associated with an allergic disease.

22. The method of claim 21, wherein said allergic disease is selected from the group consisting of asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

* * * * *